US008759316B2

(12) United States Patent
Ruderman Chen et al.

(10) Patent No.: US 8,759,316 B2
(45) Date of Patent: *Jun. 24, 2014

(54) MAINTENANCE OF PLATELET INHIBITION DURING ANTIPLATELET THERAPY

(71) Applicant: The Medicines Company, Parsippany, NJ (US)

(72) Inventors: Lisa Ruderman Chen, Rye, NY (US); Simona Skerjanec, Basel (CH); Dawn Bell, Morristown, NJ (US); Jayne Prats, Carlisle, MA (US); Meredith Todd, Hoboken, NJ (US); Clive Arthur Arculus-Meanwell, Bernardsville, NJ (US); Diane Mould, Fort Meyers, FL (US)

(73) Assignee: The Medicines Company, Parsippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/931,384

(22) Filed: Jun. 28, 2013

(65) Prior Publication Data

US 2013/0303478 A1 Nov. 14, 2013

Related U.S. Application Data

(63) Continuation-in-part of application No. 13/209,271, filed on Aug. 12, 2011, which is a continuation-in-part of application No. 12/990,332, filed as application No. PCT/US2009/043820 on May 13, 2009, application No. 13/931,384, which is a continuation-in-part of application No. 13/904,778, filed on May 29, 2013, which is a continuation-in-part of application No. 13/792,056, filed on Mar. 9, 2013, which is a continuation-in-part of application No. 12/943,717, filed on Nov. 10, 2010.

(60) Provisional application No. 61/127,414, filed on May 13, 2008, provisional application No. 61/260,361, filed on Nov. 11, 2009, provisional application No. 61/815,735, filed on Apr. 25, 2013.

(51) Int. Cl.
*A61K 31/70* (2006.01)
*C07H 19/00* (2006.01)
*C07H 19/04* (2006.01)
*C07H 19/10* (2006.01)
*C07H 19/20* (2006.01)

(52) U.S. Cl.
USPC ........ 514/47; 514/327; 536/26.23; 536/26.26; 536/26.7; 536/26.8

(58) Field of Classification Search
None
See application file for complete search history.

(56) References Cited

U.S. PATENT DOCUMENTS

| 4,529,596 | A | * | 7/1985 | Aubert et al. ............... 514/233.8 |
| 5,288,726 | A | * | 2/1994 | Koike et al. ................... 514/301 |
| 5,721,219 | A | * | 2/1998 | Ingall et al. ..................... 514/47 |
| 5,955,447 | A | | 9/1999 | Ingall |
| 6,114,313 | A | | 9/2000 | Bland |
| 6,130,208 | A | | 10/2000 | Broadhead |
| 6,693,115 | B2 | * | 2/2004 | Asai et al. ..................... 514/301 |
| 6,861,424 | B2 | | 3/2005 | Bryant |
| 2006/0121086 | A1 | | 6/2006 | Boyer et al. |
| 2006/0270607 | A1 | | 11/2006 | Dixon |
| 2007/0082840 | A1 | * | 4/2007 | Porter et al. ...................... 514/9 |
| 2007/0254324 | A1 | | 11/2007 | Rechner |
| 2011/0112030 | A1 | | 5/2011 | Arculus-Meanwell et al. |
| 2011/0288043 | A1 | | 11/2011 | Chen et al. |
| 2012/0141468 | A1 | | 6/2012 | Chen et al. |
| 2013/0040898 | A1 | | 2/2013 | Johansson et al. |
| 2013/0190265 | A1 | | 7/2013 | Arculus-Meanwell et al. |

FOREIGN PATENT DOCUMENTS

| WO | WO-2005-097814 | 10/2005 |
| WO | WO-2006-119507 | 11/2006 |
| WO | WO-2007-024472 | 3/2007 |
| WO | WO-2011/134478 A2 | 11/2011 |
| WO | WO-2013-025476 | 2/2013 |

OTHER PUBLICATIONS (R) Porter et al. (eds.), A portion of "Coronary Artery Disease," Chapter 210 in The Merck Manual of Diagnosis and Therapy, 19th Edition, Merck & Co., Inc., Rahway, NJ, 2011, only title pages and text pp. 2087-2110 supplied.*
(S) Beers et al. (eds.), "Coronary Artery Disease," Chapter 73 in The Merck Manual of Diagnosis and Therapy, 18th Edition, Merck & Co., Inc., Rahway, NJ, Jan. 2006, only title pages and text pp. 626-652 supplied.*
(T) Dovlatova et al., "Competition Between Reversible and Irreversible P2Y12 Antagonists and Its Influence on ADP-Mediated Platelet Activation," Journal of Thrombosis and Haemostasis, 5(Suppl. 2), Abstract No. S-340 (2007), only Abstract supplied.*
(U) Storey et al., "Comparison of the Pharmacodynamic Effects of the Platlet ADP Receptor Antagonists Clopidogrel and AR-C69931MX (aka Cangrelor) in Patients with Ischaemic Heart Disease," Platelets, 13, 407-413 (2002).*
(V) Kunapuli et al., ADP Receptors-Targets of Developing Antithrombotic Agents, Current Pharmaceutical Design, 9(28), 2303-2316 (2003).*
U.S. Appl. No. 13/391,287, filed Jun. 28, 2013, Ruderman Chen et al.
U.S. Appl. No. 13/904,778, filed May 29, 2013, Arculus-Meanwell et al.

(Continued)

*Primary Examiner* — Lawrence E Crane
(74) *Attorney, Agent, or Firm* — Frommer Lawrence & Haug LLP; Sandra Kuzmich, Esq.; Russell A. Garman, Esq.

(57) ABSTRACT

A method for reducing or maintaining platelet inhibition in a patient by administering cangrelor prior to an invasive procedure is described. The method of this invention can be used for patients in need of antiplatelet therapy or at risk of thrombosis. The method can further be used in patients who were previously treated with long-acting platelet inhibitors without increasing the risk of excessive bleeding.

28 Claims, 12 Drawing Sheets

(56) References Cited

OTHER PUBLICATIONS

U.S. Appl. No. 13/954,843, filed Jul. 30, 2013, Ruderman Chen et al.

Firstenberg, M.S., et al., P4-Safety and Efficacy of Cangrelor, An Intravenous, Short-Acting Platelet Inhibitor in Patients Requiring Cardiac Surgery, American Association for Thoracic Surgery, 2012.

Ahrens, I., et al., Novel antiplatelet therapies following percutaneous coronary interventions, Current Opinion in Investigational Drugs, 2009, pp. 902-911, vol. 10, No. 9.

Angiolillo, D.J., et al., Bridging antiplatelet therapy with cangrelor in patients undergoing cardiac surgery: a randomized controlled trial, Supplementary Online Content, JAMA, 2012, pp. 265-274, vol. 307, No. 3.

Angiolillo, D.J., et al., Bridging Antiplatelet Therapy With Cangrelor in Patients Undergoing Cardiac Surgery: A Randomized Controlled Trial, Original Contribution, JAMA, 2012, pp. 265-274, vol. 307, No. 3.

Angiolillo, D.J., et al., Pharmacodynamic effects of cangrelor and clopidogrel: the platelet function substudy from the cangrelor versus standard therapy to achieve optimal management of platelet inhibition (CHAMPION) trials, J.Thromb Thr., 2012, pp. 44-55, vol. 34.

Becker, R.C., et al., Management of Platelet-Directed Pharmacotherapy in Patients With Atherosclerotic Coronary Artery Disease Undergoing Elective Endoscopic Gastrointestinal Procedures, JACC, 2009, pp. 2261-2276, vol. 54, No. 24.

Desai, N. R., et al., The State of Periprocedural Antiplatelet Therapy After Recent Trials, JACC: Cardiovascular Interventions, 2010, pp. 571-583, vol. 3, No. 6.

Sabatine, M.S., Novel antiplatelet strategies in acute coronary syndromes, Cleve Clin J Med, 2009, pp. S8-S15, vol. 76, Supp. 1.

Siddique, A., et al., New antiplatelet drugs: beyond aspirin and clopidogrel, Int. J. Clin. Pract., 2009, pp. 776-789, vol. 63, No. 5.

Norgard, N.B., Cangrelor: a novel $P2Y_{12}$ receptor antagonist, Expert Opin. Investig. Drugs, 2009, pp. 1219-1230, vol. 18, No. 8.

Oestreich, J.H., et al., Cangrelor in percutaneous coronary intervention, Expert Rev. Clin. Pharmacol., 2009, pp. 137-145, vol. 2, No. 2.

Paikin, J.S., et al., New antithrombotic agents—insights from clinical trials, Nature Reviews-Cardiology, 2010, pp. 498-509, vol. 7.

Ferreiro, J.L., et al., Cangrelor: a review on its mechanism of action and clinical development, Expert Rev. Cardiovasc. Ther., 2009, pp. 1195-1201, vol. 7, No. 10.

Akers, W.S., et al., Pharmacokinetics and Pharmacodynamics of a Bolus and Infusion of Cangrelor: A Direct, Parenteral P2Y12 Receptor Antagonist, The J Clin. Pharmacol, 2009, pp. 26-35, vol. 50.

Angiolillo, D.J., et al., Clinical overview of promising nonthienopyridine antiplatelet agents, AHJ, 2008, pp. S23-S28, vol. 156, No. 2, Supp. 1.

Bassand, J-P, Unmet needs in antiplatelet therapy, EHJ Supplements, 2008, pp. D3-D11, vol. 10, Supp. D.

Dalal, A.R., et al., Brief review: Coronary drug-eluting stents and anesthesia, Can J Anesth, 2006, pp. 1230-1243, vol. 53, No. 12.

Diaz-Ricart, M., et al., Cangrelor Tetrasodium, Drugs of the Future, 2008, pp. 101-110, vol. 33, No. 2.

Fugate, S.E., et al. Cangrelor for Treatment of Coronary Thrombosis, The Annals of Pharmacotherapy, 2006, pp. 925-930, vol. 40.

Greenbaum, A.B., et al., Initial experience with an intravenous $P2Y_{12}$platelet receptor antagonist in patients undergoing percutaneous coronary intervention: Results from a 2-part, phase II, multicenter, randomized, placebo- and active-controlled trial, AHJ, 2006, pp. 689.e1-689.e10, vol. 151, No. 3.

Greenbaum, A.B., et al., Preliminary experience with intravenous $P2Y_{12}$platelet receptor inhibitions as an adjunct to reduced-dose alteplase during acute myocardial infarction: Results of the Safety, Tolerability and Effect on Patency in acute Myocardial Infarction (STEP-AMI) angiographic trial, 2007, pp. 702-709, vol. 154, No. 4.

Steinhubl, S., et al., Optimizing Platelet $P2Y_{12}$ Inhibition for Patients Undergoing PCI, Cardiovascular Drug Reviews, 2007, pp. 188-203, vol. 25, No. 2.

Krajewski, S., et al., Short-acting $P_2Y_{12}$ blockade to reduce platelet dysfunction and coagulopathy during experimental extracorporeal circulation and hypothermia, BJA, 2012, pp. 912-921, vol. 108, No. 6.

Testa, L., et al., Current Concepts on Antiplatelet Therapy: Focus on the Novel Thienopyridine and Non-Thienopyridine Agents, Advances in Hematology, 2010, pp. 1-7, vol. 2010, Article ID 595934.

Ueno, M., et al., Update on the clinical development of cangrelor, Expert Rev Cardiovasc Ther, 2010, pp. 1069-1077, vol. 8, No. 8.

Xiang, B., et al., The $P2Y_{12}$ Antagonists, 2MeSAMP and Cangrelor, Inhibit Platelet Activation through $P2Y_{12}/G_i$-Dependent Mechanism, PLOS One, 2012, pp. 1-10, vol. 7, Issue 12.

Straub, A., et al., Evidence of Platelet Activation at Medically Used Hypothermia and Mechanistic Data Indicating ADP as a Key Mediator and Therapeutic Target, JAHA, 2011, pp. 1607-1616.

Oliphant, C.S., et al., Emerging $P2Y_{12}$ Receptor Antagonists: Role in Coronary Artery Disease, Current Vascular Pharmacology, 2010, pp. 93-101, vol. 8, No. 1.

Firstenberg, M.S., et al., Safety and Efficacy of Cangrelor, an Intravenous, Short-Acting Platelet Inhibitor in Patients Requiring Coronary Artery Bypass Surgery, The Heart Surgery Forum, 2013, pp. E60-E69, vol. 16, No. 2.

Bhatt, D.L., et al., Effect of Platelet Inhibition with Cangrelor during PCI on Ischemic Events, Original Article, N Engl J Med, 2013, pp. 1303-1313, vol. 368, No. 14.

Bhatt, D.L., et al., Effect of platelet inhibition with cagrelor during PCI on ischemic events, 2013, N Engl J Med, pp. 1-15. Supplementary Appendix, Champion Phoenix.

White, H.D., et al., Reduced immediate ischemic events with cangrelor in PCI: A pooled analysis of the CHAMPION trials using the universal definition of myocardial infarction, AHJ, 2012, pp. 182-190e4, vol. 163, No. 2.

Leonardi, S.L., et al., Rationale and design of the Cangrelor versus standard therapy to achieve optimal Management of Platelet InhibitiON PHOENIX trial, AHJ, 2012 pp. 768-776.e2, vol. 163, No. 5.

Harrington, R.A., et al., Platelet Inhibition with Cangrelor in Patients Undergoing PCI, N Engl J Med, 2009, pp. 2318-2329, vol. 361, No. 24.

Bhatt, D.L., et al., Intravenous Platelet Blockade with Cangrelor during PCI, N Engl J Med, 2009, pp. 2330-2341, vol. 361, No. 24.

Bellemain-Appaiz, A., et al., New $P2Y_{12}$ Inhibitors Versus Clopidogrel in Percutaneous Coronary Intervention, JACC, 2010, pp. 1542-1551, vol. 56, No. 19.

Faxon, D.P., Cangrelor for ACS—lessons from the CHAMPION trials, Nature Reviews-Cardiology, 2010, pp. 124-125, vol. 7.

Angiolillo, D.J., ADP Receptor Antagonism—What's in the Pipeline?, Am J Cardiovasc Drugs, 2007, pp. 423-432, vol. 7, No. 6.

Humphries, R.G., Pharmacology of AR-C69931MX and related compounds: from pharmacological tools to clinical trials, 2000, Haematologica, pp. 66-72, vol. 85, (the platelet ADP receptors supplement).

Price, M.J., New antiplatelet therapies in development, 2008, Am J Health-Syst-Pharm, pp. S11-S15, vol. 65, Supp. 5.

Raju, N.C., et al., Platelet ADP-receptor antagonists for cardiovascular disease: past, present and future, 2008, pp. 766-780, vol. 5, No. 12.

Rich, J.D., et al., New antiplatelet therapies for acute coronary syndromes, 2007, Current Cardiology Reports, pp. 303-311, vol. 9.

Steinhubl, S.R., et al., Transitioning patients from cangrelor to clopidogrel: Pharmacodynamic evidence of a competitive effect, 2008, Thrombosis Research, pp. 527-534, vol. 121.

Storey, R.F., The $P2Y_{12}$ receptor as a therapeutic target in cardiovascular disease, 2001, Platelets, pp. 197-209, vol. 12.

Van Giezen, J.J.J., et al., Preclinical and clinical studies with selective reversible direct $P2Y_{12}$ Antagonists, 2005, Seminars in thrombosis and hemostasis, pp. 195-204, vol. 31, No. 2.

Examination Report issued on Aug. 21, 2013 in the related European Application No. 09747490.2.

Office Action issued on Jun. 4, 2013 in the related Chinese Application No. 200980126678.1.

Office Action issued on Jun. 11, 2013 in the related Japanese Application No. 2011-509659.

Storey, R.F., et al., Inhibition of Platelet Aggregation by AZD6140, A Reversible Oral P2Y12 Receptor Antagonist, Compared with Clopidogrel in Patients with Acute Coronary Syndromes, JACC, 2007, pp. 1852-1856, vol. 50, No. 19.

(56) References Cited

OTHER PUBLICATIONS

Gurbel, P., et al., Oral Dosing of PRT060128, a Novel Direct-Acting, Reversible-P2Y(12) Antagonist Overcomes High Platelet Reactivity in Patients Non-Responsive to Clopidogrel Therapy, Circulation, 2008, p. S972, vol. 118, No. 18.

Lepantalo A., et al., Antiplatelet Effect of Clopidogrel in Patients with Aspirin Therapy Undergoing Percutaneous Coronary Interventions—Limited Inhibition of the P2Y12 Receptor, Thromb. Res., 2009, pp. 193-198, vol. 124, No. 2.

Brilakis et al., Perioperative Management of Patients with Coronary Stents, JACC, 2007, pp. 2145-2150, vol. 49.

Bonello, et al., Consensus and Future Directions on the Definition of High On-Treatment Platelet Reactivity to Adenosine Diphosphate, JACC, 2010, pp. 919-933, vol. 56.

Price, et al., Standard- vs High-Dose Clopidogrel Based on Platelet Function Testing After Percutaneous Coronary Intervention, JAMA, 2011, pp. 1097-1105, vol. 305, No. 11.

Gurbel, et al., Peri-Operative Platelet Function Testing: The Potential for Reducing Ischaemic and Bleeding Risks, Thromb. Haemost., 2011, pp. 248-252, vol. 106.

Accumetric, LLC, VerifyNow User System User Manual, 2009.

Voisin, et al., Are P2Y12 Reaction Unit (PRU) and % Inhibition Index Equivalent for the Expression of P2Y12 Inhibition by the VerifyNow® Assay? Role of Haematocrit and Haemoglobin Levels, Thromb. Haemost, 2011, pp. 227-229, vol. 106.

International Search Report and Written Opinion by the International Searching Authority, issued on Jun. 30, 2009, in the PCT Application No. PCT/US09/43820.

International Search Report and Written Opinion by the International Searching Authority, issued on Jun. 11, 2009, in the PCT Application No. PCT/US09/42681.

Extended European Search Report issued on Apr. 11, 2012 in the related European Application No. 09747490.2.

International Search Report and Written Opinion by the International Searching Authority, issued on Jan. 3, 2014, in the PCT Application No. PCT/US2013/048735.

Angiolillo DJ, et al., Randomized Comparison of a High Clopidogrel Maintenance Dose in Patients with Diabetes Mellitus and Coronary Artery Disease, Circulation, 2007, 708-716, 115.

\* cited by examiner

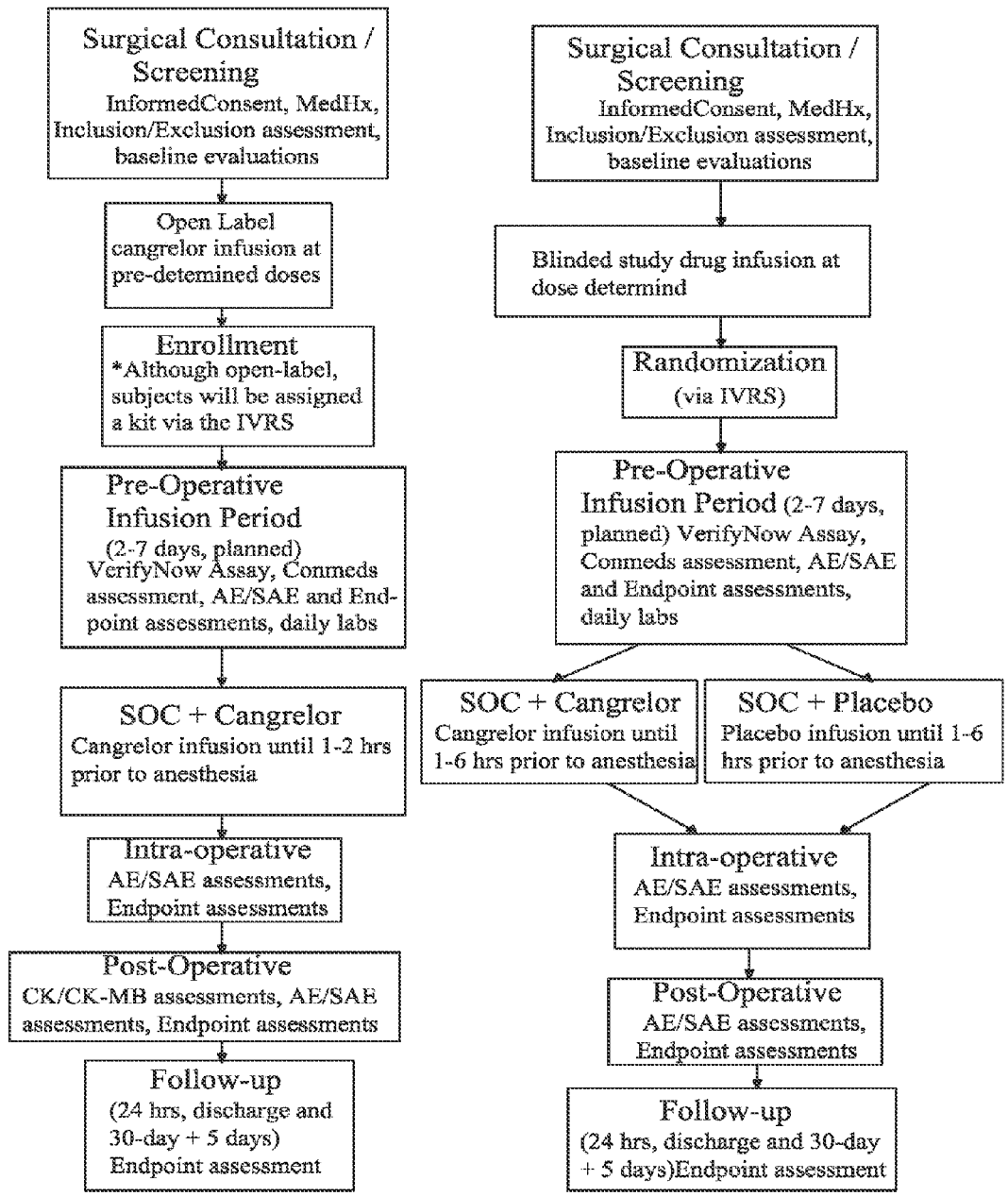
Figure 3: Chart of an Exemplary Method

Table 1: Schedule of Assessments

| Study Assessment | Screening/Randomization Pretreatment/Screening Period[1] | Pre-operative Randomization | Pre-operative Days 1-7 | Pre-operative Pre-surgery | Intra-operative During surgery[2] | Post-Operative through Discharge Immediately Post Surgery | Post-Operative through Discharge 4 h (±1 h) post surgery | Post-Operative through Discharge 24-h (±1 hr) post surgery | Post-Operative through Discharge Discharge | FUP 30-d FUP (+5 d) |
|---|---|---|---|---|---|---|---|---|---|---|
| Informed consent | X | | | | | | | | | |
| Medical History | X | | | | | | | | | |
| Review of inclusion/exclusion criteria | X | | | | | | | | | |
| Pregnancy test (serum or urine), if applicable | X | | | | | | | | | |
| PT/INR | X | | | | | | | | | |
| Previous medications | X | | | | | | | | | |
| Hematology (Hgb, Hct, WBC, platelets) | X | | X[4] | | | | | X | | |
| Serum creatinine and LFTs | X | | | | | | | | | |
| 12-lead ECG | X | | | | | | | | X | |
| CK, CK-MB | X | | | | | | | X | | |
| IVRS randomization | | X[11] | | | | | | | | |
| VerifyNow™ P2Y$_{12}$ Assay | | X[6] | X[7] | X[8] | X[9] | | | X | | |
| Study Drug Administration | | X | X | X[10] | | | | | | |
| Concomitant Medications | ←――――――――――――――――――→ | | | | | X | | | | |
| Clinical Endpoint Assessments | | | | | | X | | | | |
| Adverse Event Reporting | ←――――――――――――――――――――――――――――→ | | | | | X | | | | |
| SAE Reporting | ←――――――――――――――――――→ | | | | | X | | | | |

Figure 4-1: Table of Studied Assessments by Time Point

[1] Screening Period tests are to be conducted within 24 hours prior to randomization.
[2] Surgery start is defind as time of first incision; surgery stop is defind as last suture placed
[3] Immediately is defind as within 1 hour post end of CABG surgery unless otherwise defined
[4] Hematology tests are to be drawn daily during the infusion period, at approximately the same time each day
[5] Pre-surgery serum creatinine and LFTs should be drawn following the discontinuation of study drug infusion, but prior to CABG surgery
[6] VerifyNow™ P2Y$_{12}$ Assay sample to be drawn just prior to initiation of study drug
[7] VerifyNow™ P2Y$_{12}$ Assay samples are to be taken daily during the infusion period should be at approximately the same time each day, in conjunction with daily labs if possible
[8] Pre-surgery VerifyNow™ P2Y$_{12}$ Assay testing should be done prior to discontinuation of study drug infusion. Patients must have a minimum of 48 hours on cangrelor infusion prior to termination. If the last on-infusion VerifyNow sample was within 12 hours of study drug discontinuation, an additional draw is not required prior to termination of cangrelor
[9] VerifyNow™ P2Y$_{12}$ Assay sample to be drawn just prior to surgical incision.
[10] Study drug infusion should be stopped at no less than 1 and no more than 6 hours prior to anesthesia for surgery.
[11] IVRS randomization not appliable to Stage I. Patients will be enrolled via a manual process.

Figure 4-2: Table of Studied Assessments by Time Point

MAINTENANCE OF PLATELET INHIBITION DURING ANTIPLATELET THERAPY

CROSS REFERENCE TO RELATED APPLICATIONS

This invention is a continuation-in-part of U.S. application Ser. No. 13/209,271 filed on Aug. 12, 2011, which is a continuation-in-part of U.S. application Ser. No. 12/990,332 filed on Aug. 15, 2011, which is a National Stage Entry of PCT/US09/043,820 filed on May 13, 2009, which claims priority to U.S. provisional application Ser. No. 61/127,424 filed on May 13, 2008. This invention is also a continuation-in-part of U.S. application Ser. No. 13/904,778 filed on May 29, 2013, which is a continuation-in-part of U.S. application Ser. No. 13/792,056 filed on Mar. 9, 2013, which is a continuation-in-part of U.S. application Ser. No. 12/943,717 filed on Nov. 10, 2010, which claims priority to U.S. provisional application Ser. No. 61/260,361 filed on Nov. 11, 2009. U.S. application Ser. No. 13/904,778 also claims priority to U.S. provisional application Ser. No. 61/815,735 filed on Apr. 25, 2013. Each of the above-referenced applications is incorporated herein by reference.

FIELD OF THE INVENTION

The instant invention relates to the field of platelet inhibition, and in particular to methods of maintaining or reducing platelet activity in patients undergoing an invasive procedure.

BACKGROUND OF THE INVENTION

Antiplatelet therapy has been shown to reduce clinical ischemic events and improve outcomes for acute coronary syndrome (ACS) patients. Currently, the approved antiplatelet products include aspirin and thienopyridines, such as clopidogrel and ticlopidine. One of the most widely prescribed thienopyridines is clopidogrel, which is also known as Plavix®.

Thienopyridines such as clopidogrel irreversibly inhibit $P2Y_{12}$ receptors, which play an active role in platelet activation. In the normal state, when blood vessels are damaged, platelet activation mediated by $P2Y_{12}$ receptors play an important role to arrest bleeding at the site of injury. In a diseased state, platelet activation leads to vascular occlusion and ischemic damage. Thus, $P2Y_{12}$ receptor antagonists play a key role in antiplatelet therapy in assisting to prevent coronary artery disease and for the immediate treatment of ACS and percutaneous coronary intervention (PCI).

Physicians often prescribe dual antiplatelet therapy, which include aspirin and a thienopyridine such as clopidogrel, as a first line treatment for patients who have been diagnosed with ACS or who are showing symptoms associated with ACS. Pending further examinations, these patients may continue with this treatment or receive other treatments such as coronary artery bypass grafting (CABG) and PCI. Consistent with this practice, current American College of Cardiology/American Heart Association (ACC/AHA) guidelines recommend immediate initiation of dual antiplatelet therapy of clopidogrel and aspirin after a patient is diagnosed with ACS. Similarly, patients who have received a bare metal stent or drug-eluting stent are also put on the dual clopidogrel and aspirin therapy for an extended period of time to prevent an ischemic event. For instance, a post hoc analysis of a blinded, placebo-controlled trial suggests a benefit of platelet activity inhibition in terms of decreased thrombotic events prior to CABG (Fox K A et. al, Circulation. 2004; 110; 1201-08). For many patients, this dual antiplatelet therapy provides tremendous clinical benefits, and minimizes the risks of ischemic events, such as heart attack and stroke.

Dual antiplatelet therapy, however, has drawbacks. Cessation of clopidogrel may increase the incidence of ischemic events in the short-term due to a "rebound" effect of platelet activation (Brilakis E S et al, J Am Coll Cardiol. 2007 Jun. 5; 49(22): 2145-50; Ho P M et al, JAMA. 2008 Feb. 6; 299(5): 532-9).

In addition patients receiving dual antiplatelet therapy experience an increased incidence of blood transfusions and bleeding complications while undergoing surgery and other invasive procedures. This is particularly true for ACS patients who often receive surgery, such as CABG and PCI, and other invasive procedures, such as implantation of a bare metal stent (BMS) or drug-eluting stent (DES). Because aspirin and thienopyridines are irreversible, long-acting platelet antagonists, reversal of the inhibition of platelet function occurs only as new platelets are generated; therefore, even after discontinuation, their effect can last several days before being completely eliminated.

Thus, for patients under dual therapy who also require surgery such as CABG, sustained platelet inhibition poses an unacceptable risk of bleeding. Consequently, it has been recommended by the ACC/AHA and the Society of Thoracic Surgeons (STS) guidelines to cease thienopyridine therapy prior to undergoing non-emergent cardiac surgical procedures to minimize bleeding risks. Hence, patients are often required to stop dual antiplatelet therapy and wait for five to seven days before any invasive procedures can be performed.

On the other hand, even though clopidogrel treatment prior to CABG does increase bleeding due to its irreversibility, platelet $P2Y_{12}$ inhibition appears to prevent ischemic events in patients requiring CABG. As a result, physicians often face the difficult choice of discontinuing clopidogrel and aspirin prior to surgery and risking a potential ischemic event in the unprotected perioperative period or delaying surgery until the time at which clopidogrel is no longer required.

Currently, no ultra short-acting platelet inhibitors are available that allow maintenance of platelet inhibition before an invasive procedure without increasing bleeding complications at the time of the invasive procedure. Potentially, effective platelet inhibition with an ultra short-acting platelet inhibitor during the period of clopidogrel withdrawal may protect patients from ischemic events and also preserve normal hemostasis at the time of surgery.

Therefore, a need exists for a new therapy for patients who are undergoing surgery (this includes therapy prior to, during, and post) or other invasive procedures, and who have a need for antiplatelet therapy. This new therapy should maintain platelet inhibition at acceptable levels while allowing for rapid restoration of platelet function after discontinuation, thereby "bridging" patients to their surgical procedures without increasing the risk of bleeding complications.

In addition, a need exists for a new therapy for patients who, for whatever reason, cannot be administered thienopyridines, such as clopidogrel or Plavix®, or cannot receive orally administered antiplatelet therapies.

SUMMARY OF THE INVENTION

As shown herein, the present invention describes compositions and methods of maintaining or reducing platelet activity in a patient prior to the patient undergoing an invasive procedure by administering an effective amount of short-acting $P2Y_{12}$ inhibitor.

In one aspect of this invention methods are described for administering an effective amount of a short-acting $P2Y_{12}$ inhibitor to maintain or reduce platelet activity in a patient before an invasive procedure, in a patient previously treated with long-acting irreversible platelet inhibitors without an increased risk in bleeding.

In a related embodiment of this method, other therapeutic agents are administered concurrently with the reversible, short-acting $P2Y_{12}$ inhibitor.

In another related embodiment of this method, the risk of bleeding is not increased.

In another aspect of this invention, a short-acting $P2Y_{12}$ inhibitor is used to maintain or reduce platelet activity in a patient perioperatively where oral antiplatelet therapy is contraindicated. The reversible, short-acting $P2Y_{12}$ inhibitor can be administered to a patient as a bolus and/or a continuous intravenous infusion.

In another aspect of this invention, methods are described where an effective amount of a short-acting $P2Y_{12}$ inhibitor is administered to sufficiently reduce or maintain at least 60% platelet inhibition or P2Y12 reaction units (PRU) values less than 240 prior to the patient undergoing an invasive procedure.

In a related embodiment to this method, the short-acting $P2Y_{12}$ inhibitor is discontinued thereby allowing platelet activity to return to pre-administration levels as measured by PRU being greater than 240.

In yet another aspect of the present invention, methods are described for administering a reversible, short-acting $P2Y_{12}$ inhibitor to a patient who was previously administered a thienopyridine, and ceasing administration of the short-acting $P2Y_{12}$ inhibitor wherein the PRU levels are similar to pre-administration levels of the short-acting $P2Y_{12}$ inhibitor, prior to said patient undergoing an invasive procedure.

In another aspect of this invention, a method of treating or preventing thrombosis is described by administering a short-acting $P2Y_{12}$ inhibitor to a patient previously treated with a long-acting irreversible platelet inhibitor, where the risk of bleeding is not increased.

In another aspect of this invention, an intravenous pharmaceutical composition of cangrelor is described for maintaining or reducing platelet inhibition.

In another aspect of this invention, a method for preparing an intravenous cangrelor composition for inhibiting platelet activity by combining cangrelor with mannitol, sorbitol and intravenously administrable excipient for maintaining PRU values at a certain level.

Aspects of the present invention relate to a method of transitioning a patient from administration of cangrelor during PCI to administration of cangrelor in preparation for surgery, or a method of maintaining reduced platelet activity in a patient who is transitioning from administration of cangrelor during PCI to administration of cangrelor in preparation for surgery, or a method of maintaining $P2Y_{12}$ inhibition in a patient who is transitioning from administration of cangrelor during PCI to administration of cangrelor in preparation for surgery. These methods may comprise (1) administering a PCI dosing regimen, wherein the PCI dosing regimen comprises administering intravenously a 30 µg/kg bolus of cangrelor before the start of PCI, and administering intravenously a continuous infusion of cangrelor at an infusion rate of 4 µg/kg/min after administration of the bolus; (2) discontinuing the administration of the PCI dosing regimen; and (3) administering a bridge dosing regimen, wherein the bridge dosing regimen comprises administering intravenously a continuous infusion of cangrelor at an infusion rate of 0.75 µg/kg/min.

Aspects of the present invention further relate to a method of transitioning a patient from administration of cangrelor in preparation for surgery to administration of cangrelor during PCI, or a method of maintaining reduced platelet activity in a patient who is transitioning from administration of cangrelor in preparation for surgery to administration of cangrelor during PCI, or a method of maintaining $P2Y_{12}$ inhibition in a patient who is transitioning from administration of cangrelor in preparation for surgery to administration of cangrelor during PCI. These methods may comprise (1) administering a bridge dosing regimen, wherein the bridge dosing regimen comprises administering intravenously a continuous infusion of cangrelor at an infusion rate of 0.75 µg/kg/min; (2) discontinuing the administration of the bridge dosing regimen; and (3) administering a PCI dosing regimen, wherein the PCI dosing regimen comprises administering intravenously a 30 µg/kg bolus of cangrelor before the start of PCI, and administering intravenously a continuous infusion of cangrelor at an infusion rate of 4 µg/kg/min. In another embodiment, the method may comprise (1) administering a bridge dosing regimen, wherein the bridge dosing regimen comprises administering intravenously a continuous infusion of cangrelor at an infusion rate of 0.75 µg/kg/min; (2) discontinuing the administration of the bridge dosing regimen; and (3) administering a PCI dosing regimen, wherein the PCI dosing regimen comprises administering intravenously a continuous infusion of cangrelor at an infusion rate of 4 µg/kg/min.

BRIEF DESCRIPTION OF THE FIGURES

Understanding of the present invention will be facilitated by consideration of the following detailed description of the embodiments of the present invention taken in conjunction with the accompanying drawings, in which like numerals refer to like parts and in which:

FIG. 3 is a flow chart of a study demonstrating an exemplary method;

FIGS. 4-1 and 4-2 show a table of the studied assessments by time point;

DETAILED DESCRIPTION OF THE INVENTION

Figure 1:
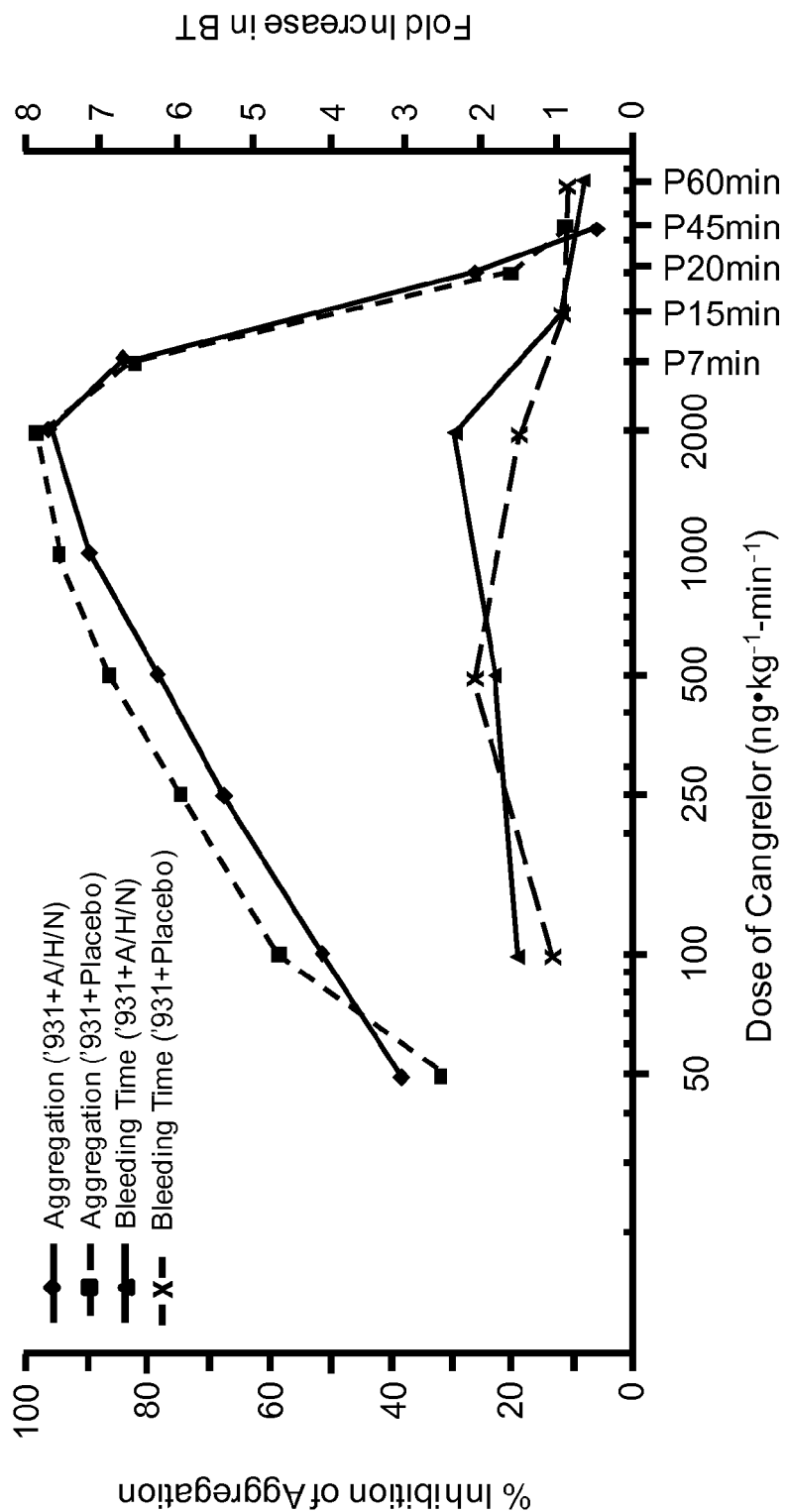
FIG. 1 is a graphical presentation of the percent inhibition of adenosine diphosphate (ADP)-induced platelet aggregation and effect on bleeding time.

It is to be understood that the figures and descriptions of the present invention have been simplified to illustrate elements that are relevant for a clear understanding of the present invention, while eliminating, for the purpose of clarity, many other elements found in typical antiplatelet therapies. Those of ordinary skill in the art will recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art. Furthermore, the embodiments identified and illustrated herein are for exemplary purposes only, and are not meant to be exclusive or limited in their description of the present invention.

The present invention provides a method for inhibiting platelet reactivity in patients prior to undergoing an invasive procedure.

The methods described in the present invention maintains platelet inhibition at acceptable and targeted levels, while allowing for rapid restoration of platelet function after discontinuation of the drug therapy so that patients may undergo invasive procedures without increasing the risk of bleeding complications.

The described methods can be used for patients in need of treatment to reduce or maintain platelet inhibition. Preferably the described methods can be used in patients at risk of thrombotic events. More preferably the embodiments of the present invention are directed to patients diagnosed with symptoms of stable or unstable angina, vascular ischemic events, atherosclerosis, acute coronary syndrome, as well as ST-elevation myocardial infarction (STEMI) or non-ST segment elevation myocardial infarction (N-STEMI). The described methods can also be used for patients having previously received a stent, such as a bare metal stent or a drug-eluting stent, for the treatment or prevention of stent thrombosis. While the present invention is generally targeted for use with human patients, the described methods can be used on any living animal.

The present invention further provides a method for reducing or maintaining adequate $P2Y_{12}$ inhibition with rapid reversibility upon discontinuation of long-acting irreversible platelet inhibitors prior to patients undergoing invasive procedures without increasing the risk of bleeding complications.

DEFINITIONS

Long-acting $P2Y_{12}$ inhibitors refer to compounds which inhibit $P2Y_{12}$ receptor activities, having a slow on-set and long elimination half-life. Examples of long-acting $P2Y_{12}$ inhibitors are typically formulated as oral dosage forms. One example of long-acting $P2Y_{12}$ inhibitor is long-acting irreversible $P2Y_{12}$ inhibitors. Examples of long-acting irreversible $P2Y_{12}$ inhibitors include thienopyridines. Examples of thienopyridines include, without limitation, clopidogrel, ticloridine, and prasugrel and such other compounds having similar properties. Clopidogrel is a pro-drug that requires metabolism for conversion to the active metabolite.

Short-acting reversible, $P2Y_{12}$ inhibitors refer to compounds which inhibits $P2Y_{12}$ receptor activities, having a fast onset time and a relatively short metabolism rate as compared to those of thienopyridines. Examples of a short-acting, reversible $P2Y_{12}$ inhibitor include, without limitations, cangrelor, ticagrelor and PRT060128. It should be noted that the present invention is not limited to these examples. Additional compounds that have similar properties may also be used in the present invention.

One particularly preferred example of a reversible, short-acting $P2Y_{12}$ inhibitor is cangrelor. Cangrelor is a potent, direct, and reversible antagonist of the platelet $P2Y_{12}$ receptor. Cangrelor has a half-life of approximately less than 10 minutes, allowing for a return to normal platelet function in a very short period of time upon discontinuation of the drug. By reducing the need for a compound to be metabolized for activity, and by having a relatively short half-life, reversible, short-acting $P2Y_{12}$ inhibitors are considered "reversible," meaning that full platelet functionality may return rather quickly as compared to thienopyridines.

The binding of cangrelor to the $P2Y_{12}$ receptor inhibits platelet activation as well as aggregation when mediated in whole or in part via this receptor. Cangrelor can be derived completely from synthetic materials, and is an analogue of adenosine triphosphate (ATP). ATP is a natural antagonist of the $P2Y_{12}$ receptor sites and is found in humans.

The chemical structure for cangrelor is depicted below as Formula I.

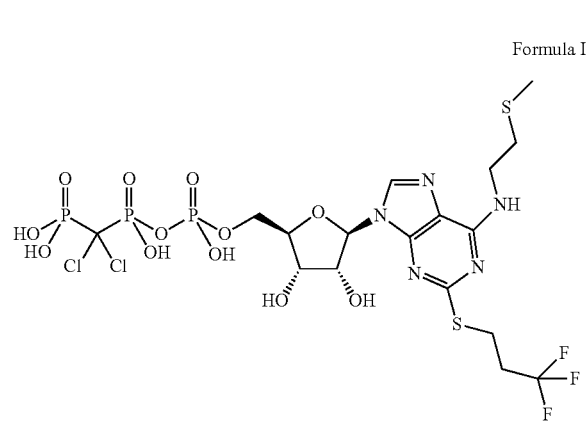 [SMILES: CSCCNc1nc(SCCC(F)(F)F)nc2c1ncn2[C@@H]1O[C@H](COP(=O)(O)OP(=O)(O)C(Cl)(Cl)P(=O)(O)O)[C@@H](O)[C@H]1O]

Formula I

Cangrelor is clinically well tolerated and safe and has no drug-drug interaction with aspirin, heparin or nitroglycerin. Unlike orally dosed thienopyridines, cangrelor can be administered intravenously and binds directly to $P2Y_{12}$ receptor sites of platelets. In each of the embodiments of the present invention, the term "cangrelor" encompasses the compound of Formula I as well as tautomeric, enantiomeric and diastereomeric forms thereof, and racemic mixtures thereof, other chemically active forms thereof, and pharmaceutically acceptable salts of these compounds, including a tetrasodium salt. These alternative forms and salts, processes for their production, and pharmaceutical compositions comprising them, are well known in the art and set forth, for example, in U.S. Pat. No. 5,721,219. Additional disclosure relevant to the production and use of cangrelor may be found in U.S. Pat. Nos. 5,955,447, 6,130,208 and 6,114,313, as well as in U.S. Appln. Publication Nos. 2006/0270607 and 2011/0112030.

Invasive procedures means any technique where entry to a body cavity is required or where the normal function of the body is in some way interrupted by a medical procedure and/or treatment that invades (enters) the body, usually by cutting or puncturing the skin and/or by inserting instruments into the body. Invasive procedures can include CABG, orthopedic surgeries, urological surgeries, PCI, other general invasive procedures, such as endarterectomy, renal dialysis, cardio-pulmonary bypass, endoscopic procedures or any medical, surgical, or dental procedure that could result in excessive bleeding or hemorrhage to the patient.

Perioperative means the period of a patient's invasive procedure which can occur in hospitals, surgical centers or health care providers' offices. Perioperative includes admission, anesthesia, surgery, to recovery.

Thrombosis is the formation of a blood clot (thrombus) inside a blood vessel obstructing the flow of blood through the circulatory system. When a blood vessel is injured, the body uses platelets and fibrin to form a blood clot to prevent blood loss. Some examples of the types of thrombosis include venous thrombosis which includes deep vein thrombosis, portal vein thrombosis, renal vein thrombosis, jugular vein thrombosis, Budd-Chiari syndrome, Paget-Schroetter disease, cerebral venous sinus thrombosis, cerebral venous sinus thrombosis and arterial thrombosis which includes stroke and myocardial infarction.

Dosage and Administration

As used herein, the terms "dose", "dosage", "unit dose", "unit dosage", "effective dose", "effective amount" and related terms refer to physically discrete units that contain a predetermined quantity of cangrelor, calculated to produce a desired therapeutic effect. These terms are synonymous with the therapeutically effective amounts and amounts sufficient to achieve the stated goals of the methods disclosed herein.

When administered as an IV formulation, a pharmaceutical composition comprising cangrelor may be administered as a bolus, as a continuous infusion, or as a bolus followed by a continuous infusion. When administered as a bolus, a dose of about 5, 10, 15, 20, 25, 30, 35, 40, 45, 50, 55, 60, 65, 70, 75, 80, 85, 90, 95 or 100 µg/kg cangrelor, or more, is administered to the patient. In preferred embodiments, between about 20 µg/kg and about 40 µg/kg cangrelor is administered, more preferably about 30 µg/kg. When administered as a continuous infusion, cangrelor may be administered at about 0.1, 0.5, 0.75, 1, 2, 3, 4, 5, 6, 7, 8, 9, 10, 15, 20, 25, 30 µg/kg/min, or more to the patient. In preferred embodiments, between about 0.1 and about 5 µg/kg/min cangrelor is administered, more preferred is administration of cangrelor in the range of about 0.5 µg/kg/min to about 2 µg/kg/min. Even more preferred is a dosage range of cangrelor at about 0.5 µg/kg/min to about 1 µg/kg/min. The skilled artisan will understand that different bolus and intravenous dosages from those set forth here may be administered based on the particular characteristic of the patient. Thus, the dosage amount can be varied from the dosage amount presently described, however, the dosage given must be sufficient to reduce or maintain the PRU values below about 240 as measured by VerifyNow®.

In addition, the skilled artisan will understand that the exact amount of reversible short-acting $P2Y_{12}$ inhibitor to be administered to a patient will vary depending on the degree of platelet activity inhibition that is sought. For example, the amount of reversible short-acting $P2Y_{12}$ inhibitor to be administered to a patient during an invasive procedure that will result in bleeding may be much less than the amount that would be administered when such a procedure is not being performed.

The dosage of the reversible short-acting $P2Y_{12}$ inhibitor may be administered as a continuous intravenous infusion or it may be administered in discrete doses, such as between 1 and 48 doses, or more, per 24 hour period. The dosage of the reversible short-acting $P2Y_{12}$ inhibitor may vary over time, with a lower dosage being initially administered, followed by an increased dosage for a sustained period of time, with an optional decrease in the dosage prior to complete cessation of administration of the reversible short-acting $P2Y_{12}$ inhibitor. Such a dosing regime may be used in conjunction with the concurrent cessation of thienopyridine and/or aspirin treatment and beginning of reversible short-acting $P2Y_{12}$ inhibitor. Such dosing regime can also ensure a constant level of platelet activity inhibition.

In other forms, a reversible, short-acting $P2Y_{12}$ inhibitor can be administered at a daily dose of from 0.1 mg to 1000 mg, which may be in divided doses, e.g., up to 6 times per day.

The total amount of reversible, short-acting $P2Y_{12}$ inhibitor that may be administered to a subject may be between about 0.01 and 1000 mg per 24 hour period, with exemplary totals of about 0.5, 0.75, 1.0, 1.25, 1.5, 1.75, 2.0 and 2.5 mg per 24 hour period.

In each of the embodiments where the pharmaceutical composition is administered as continuous intravenous infusion, the infusion may continue for at least about 2 days to about 7 days. The skilled artisan will understand that the period of time over which the pharmaceutical composition is administered may be shorter or longer than the indicated times due to the particular characteristics of a patient. Administration of a reversible, short-acting $P2Y_{12}$ inhibitor can be made several days to several hours prior to the invasive procedure. One example is to administer a reversible, short-acting $P2Y_{12}$ inhibitor about 7 days to about 1 hour prior to an invasive procedure. To maintain platelet inhibition, the reversible short-acting $P2Y_{12}$ inhibitor should be administered within about 2 days to about 7 days of ceasing administration of the long-acting platelet inhibitor. A further example is to administer the reversible short-acting $P2Y_{12}$ inhibitor within about 3 days of ceasing administration of the long-acting platelet inhibitor. Discontinuation of the reversible short-acting $P2Y_{12}$ inhibitor can be performed about 1 to 6 hours before a surgical procedure. It should be noted that the duration for administering a reversible, short-acting $P2Y_{12}$ inhibitor often vary depending on which reversible, short-acting $P2Y_{12}$ inhibitor is used and the particular characteristic of the patient. One skilled in the art can vary the duration of administration so long as platelet inhibition as measured by VerifyNow® is below about 240.

Reversible, short-acting $P2Y_{12}$ inhibitors, such as cangrelor, ticagrelor or PRT060128, can be administered using any of the various methods and delivery systems known to those skilled in the art. The administering can be performed, for example, intravenously, orally, via implant, transmucosally, transdermally, intramuscularly, intrathecally, and subcutaneously. According to one preferred embodiment, a reversible, short-acting $P2Y_{12}$ inhibitor may be administered intravenously. It is contemplated that the reversible, short-acting $P2Y_{12}$ inhibitor can be administered intravenously in accordance with the present invention during surgery, when the patient is comatose, or any other such scenario where the oral administration of the inhibitor is prohibited.

In the case of administering the therapy prior to surgery in accordance with one embodiment of the present invention, such use allows patients to undergo surgery or other invasive procedures without excessive perioperative bleeding. For example, as described herein, cangrelor infusion can maintain platelet inhibition levels of approximately greater than or equal to about 60% after discontinuation of clopidogrel without an increase in bleeding risk and before the invasive procedure begins.

In addition to the pharmaceutical compositions of the present invention comprising cangrelor, the skilled artisan will understand that additional therapeutic agents may be used in combination with cangrelor. By way of non-limiting examples, compounds such as aspirin, bivalirudin, unfractionated heparin, low molecular weight heparin, fondaprinux sodium, warfarin, coumarins, thrombolytics such as streptokinase, alteplase, reteplase, urokinse, tenecteplase, glycoprotein IIb/IIIa inhibitors such as eptifibatide, abciximab, tirofiban, or antifibrinolytic agents such as epsilon aminocaproic acid, and tranexamic acid, can be used as concomitant medications.

Measurement of Platelet Activity

Assessment of platelet function can be determined by use of the VerifyNow® assay of which the System User Manual (Accumetrics, San Diego, Calif., 2009) is incorporated by reference in its entirety. The VerifyNow® P2Y12 assay is a point of care device for the assessment of the level of inhibition of platelet activation specifically designed for patients exposed to thienopyridines. It should be understood that any assay system for determining levels of inhibition of platelet activation can be used, as understood by those having skill in the art. Blood samples for the VerifyNow® P2Y12 assay can be collected into Greiner Bio-One Vacuette partial fill blood collection tubes (2 mL fill volume) containing 3.2% citrate, or by other suitable means.

The VerifyNow® P2Y12 assay is a rapid platelet-function cartridge-based assay that activates platelets using ADP, but also uses prostaglandin E1 to suppress the ADP-induced P2Y1-mediated increase in intracellular calcium levels to increase the specificity of the test for inhibition of the $P2Y_{12}$ receptor. The test cartridge contains a lyophilized preparation of human fibrinogen coated beads, platelet agonist, buffer and preservative. Fibrinogen-coated microparticles are used to bind to available platelet receptors. When the activated platelets are exposed to the fibrinogen-coated microparticles, agglutination occurs in proportion to the number of available platelet receptors. The whole-blood citrate mixture is added to the cartridge, and agglutination between platelets and coated beads is recorded. The VerifyNow® P2Y12 device is a turbidimetric optical detection system, which measures platelet induced aggregation as an increase in light transmittance. VerifyNow® P2Y12 testing can be used at any time point as described herein to assess the level of inhibition of platelet activity.

Assay results are expressed in PRU (VerifyNow® System User Manual (Accumetrics, San Diego, Calif., 2009)). High platelet reactivity, as assessed by VerifyNow® P2Y12 assay was defined as a PRU value greater than 240. The lower the PRU value, the greater the inhibition of the $P2Y_{12}$ receptor resulting in reduction of the platelet activity. For the methods described in this invention, the PRU level is preferably maintained during the period of cangrelor administration at 240 or less. In a preferred embodiment of the present invention, the dose of cangrelor was 0.75 µg/kg/min. This dose was maintained for about 2 to about 7 days. PRU values in the patients were less than or equal to 240.

It would be understood by those skilled in the art that increasing the concentration of cangrelor infusion will result in a decrease in PRU values and an increase in the percent platelet inhibition. It is therefore preferred to measure PRU values during the course of cangrelor infusion.

Pharmaceutical Compositions

In each aspect and embodiment of the present invention, short-acting reversible platelet inhibitor is administered to a patient in the form of a pharmaceutical composition comprising the active ingredient and, optionally, a pharmaceutically acceptable carrier, diluent and/or excipient. Thus, the present invention encompasses a pharmaceutical composition comprising cangrelor, and a pharmaceutically acceptable carrier, diluent and/or excipient.

Suitable carriers and diluents are well known to those skilled in the art and include saline, such as 0.9% NaCl, buffered saline, dextrose (e.g., 5% dextrose in water), water, Water-for-Injection (WFI), glycerol, ethanol, ringer's solution, propylene glycol, polysorbate 80 (Tween-80), 0.002% polysorbate 80 (Tween-80), poly(ethylene)glycol 300 and 400 (PEG 300 and 400), PEGylated castor oil (e.g. Cremophor EL), poloxamer 407 and 188, a cyclodextrin or a cyclodextrin derivative (including 2-hydroxypropyl)-cyclodextrin HPCD) and (2-hydroxyethyl)-cyclodextrin, hydrophilic and hydrophobic carriers, and combinations thereof. Hydrophobic carriers include, for example, fat emulsions, lipids, PEGylated phospholipids, polymer matrices, biocompatible polymers, liposphemers, vesicles, particles, and liposomes. Excipients included in a pharmaceutical composition have different purposes depending, for example, on the nature of the drugs, and the mode of administration. Examples of generally used excipients include, without limitation: stabilizing agents, solubilizing agents and surfactants, buffers, antioxidants and preservatives, tonicity agents, bulking agents, lubricating agents, emulsifiers, suspending or viscosity agents, inert diluents, fillers, disintegrating agents, binding agents, wetting agents, lubricating agents, antibacterials, chelating agents, sweeteners, perfuming agents, flavouring agents, coloring agents, administration aids, and combinations thereof.

The pharmaceutical composition may contain common carriers and excipients, such as cornstarch or gelatin, lactose, sucrose, microcrystalline cellulose, kaolin, mannitol, sorbiton, dicalcium phosphate, sodium chloride, alginic acid, croscarmellose sodium, and sodium starch glycolate.

The pharmaceutical compositions of the present invention may be formulated, for example, for oral, sublingual, intranasal, intraocular, rectal, transdermal, mucosal, topical or parenteral administration. Parenteral modes of administration include without limitation, intradermal, subcutaneous (s.c., s.q., sub-Q, Hypo), intramuscular (i.m.), intravenous (i.v. or IV), intraperitoneal (i.p.), intra-arterial, intramedulary, intracardiac, intra-articular (joint), intrasynovial (joint fluid area), intracranial, intraspinal, and intrathecal (spinal fluids). Any known device useful for parenteral injection or infusion of drug formulations can be used to effect such administration. In noted aspects and embodiments of the present invention, administration of the pharmaceutical compositions is via parenteral administration, preferably intravenous administration.

In IV administration, a sterile formulation of the pharmaceutical compositions of the present invention and optionally one or more additives, including solubilizers or surfactants, can be dissolved or suspended in any of the commonly used intravenous fluids and administered by infusion. Intravenous fluids include, without limitation, isotonic infusion media such as physiological saline, 0.9% NaCl, phosphate buffered saline, 5% dextrose in water, 0.002% polysorbate 80 (Tween-80) in water or Ringer's solution.

Pharmaceutical compositions comprising cangrelor of the present invention include pharmaceutical compositions comprising from about 0.1 to about 50 mg/ml of cangrelor. Particular examples of pharmaceutical compositions comprising cangrelor include the following: (i) cangrelor at a concentration of about 0.1, 0.5, 1, 2, 3, 4, 5, 6, 7, 8, 9, or 10 mg/mL in 0.9% NaCl; and (ii) cangrelor at a concentration of about 0.1, 0.5, 1, 2, 3, 4, 5, 6, 7, 8, 9, or 10 mg/mL in 5% dextrose in water. The pharmaceutical composition may further comprise a pharmaceutically acceptable carrier or diluent such as sorbitol and mannitol.

One method for preparing a cangrelor composition includes dissolving 50 mg lyophilized cangrelor or its pharmaceutically acceptable salt by injecting 5 ml sterile water into a 10 ml vial containing cangrelor or its pharmaceutically acceptable salt thereof, preparing an intravenous bag by immediately adding the dissolved cangrelor to an intravenous bag containing saline solution in volumes such as 250 ml, 500 ml, or 1000 ml of saline solution and mixing the intravenous bag thoroughly for administration. Cangrelor compositions should be prepared immediately prior to administration via infusion. It is within the skilled in the art to vary the volume of saline and amount of cangrelor in the exemplary method described above to achieve the dosage amount described in the preferred embodiments.

The described methods can be used for patients diagnosed with symptoms of conditions such as stable or unstable angina, vascular ischemic events, atherosclerosis, acute coronary syndrome, including STEMI or N-STEMI. The described methods can also be used for patients having previously received a stent, such as a bare metal stent or a drug-eluting stent, and the treatment or prevention of stent thrombosis.

The described methods can be used for a patient before, during, and after an invasive procedure, such as coronary artery bypass grafting, orthopedic surgeries, urological surgeries, percutaneous coronary intervention, other general invasive procedures, such as endarterectomy, renal dialysis, cardio-pulmonary bypass, endoscopic procedures or any medical, surgical, or dental procedure that could potentially lead to excessive bleeding or hemorrhage.

Further, the described methods of the present invention can be used in a patient who cannot be orally administered therapies and, for whatever reason, cannot be administered long lasting thienopyridines, such as clopidogrel or Plavix®.

Results of the Methods

To determine how to administer a reversible, short-acting $P2Y_{12}$ inhibitor or the amount of a reversible, short-acting $P2Y_{12}$ inhibitor to be administered, the pharmacokinetic profile of the reversible, short-acting $P2Y_{12}$ inhibitor can be analyzed using the methods well-known to a person skilled in the art.

For example, the pharmacokinetics of cangrelor has been shown to be substantially linear, and its steady-state plasma concentrations can be achieved in less than approximately 5 minutes following the administration of an intravenous infusion.

Cangrelor produced potent inhibition of ADP-induced platelet aggregation ex vivo with half maximal inhibitory concentration (IC50) 7.72+/−1.95 ng/mL. As may be seen in FIG. 1, over 80% inhibition was achieved at doses of about 0.5 µg/kg/min and above. Inhibition by cangrelor was rapidly reversible and platelet aggregation response restored close to baseline within one hour of stopping the infusion. An infusion dose of approximately about 0.75 µg/kg/min of cangrelor can also maintain adequate antiplatelet activity during infusion in the targeted patient prior to an invasive procedure.

It has been determined that consistent and complete platelet inhibition can be maintained throughout cangrelor infusion with full recovery of platelet function within approximately one hour of infusion cessation. Clopidogrel administration at the termination of cangrelor infusion may lead to the expected degree of platelet inhibition, which may be measured by P-selectin expression, electrical impedance and light transmittance aggregometry.

Transition from PCI Dosing Regimen to Bridge Dosing Regimen, and from Bridge Dosing Regimen to PCI Dosing Regimen An aspect of the present invention is a method of transitioning a patient from administration of cangrelor during PCI to administration of cangrelor in preparation for surgery, or a method of transitioning a patient from administration of cangrelor in preparation for surgery to administration of cangrelor during PCI. Another aspect of the invention is a method of maintaining reduced platelet activity in a patient who is transitioning from administration of cangrelor during PCI to administration of cangrelor in preparation for surgery, or who is transitioning from administration of cangrelor in preparation for surgery to administration of cangrelor during PCI. Yet a further aspect of the invention is a method of maintaining $P2Y_{12}$ inhibition in a patient who is transitioning from administration of cangrelor during PCI to administration of cangrelor in preparation for surgery, or who is transitioning from administration of cangrelor in preparation for surgery to administration of cangrelor during PCI.

The reasons why a patient may have to transition from administration of cangrelor during PCI to administration of cangrelor in preparation for surgery, or vice-versa, can vary. For example, as a patient is administered cangrelor during PCI, it may be determined that surgery is necessary due to, for instance, new information that was gathered during PCI or complications that arose from the PCI procedure itself. On the other hand, a patient administered cangrelor during preparation for surgery may have to undergo PCI, such as when it is discovered that the patient is in immediate need of angioplasty or the implantation of a stent. In each of these cases, the patient has to change from one dosing regimen of cangrelor to a different dosing regimen.

Transitioning from administration of cangrelor during PCI to administration of cangrelor in preparation for surgery may be performed by administering a PCI dosing regimen, discontinuing the administration of the PCI dosing regimen, and administering a bridge dosing regimen. Transitioning from administration of cangrelor in preparation for surgery to administration of cangrelor during PCI may be performed by administering a bridge dosing regimen, discontinuing the administration of the bridge dosing regimen, and administering a PCI dosing regimen. A "PCI dosing regimen" refers to the doses of cangrelor that a patient receives when undergoing PCI. A "bridge dosing regimen" refers to the doses of cangrelor that a patient receives in the "bridging" period leading up to surgery, i.e., the period of time between the discontinuation of oral P2Y$_{12}$ inhibitors and surgery.

The PCI dosing regimen comprises administering intravenously a continuous infusion of cangrelor at a rate of about 3 to about 10 μg/kg/min, or about 4 μg/kg/min. The continuous infusion may be accompanied by intravenous administration of a bolus. The bolus may comprise about 10 to about 100 μg/kg cangrelor, such as between about 20 and about 40 μg/kg cangrelor, or about 30 μg/kg cangrelor. The bolus may be administered rapidly, for example, in less than about two minutes, or less than about one minute. Preferably, the administration of the continuous infusion is started immediately after the administration of the bolus.

The bridge dosing regimen comprises administering intravenously a continuous infusion of cangrelor at a rate of about 0.1 to about 2 μg/kg/min, or about 0.75 μg/kg/min.

The cangrelor may be administered in a pharmaceutical composition. The pharmaceutical composition may comprise 200 μg/mL of cangrelor. The pharmaceutical composition may also comprise sodium chloride injection 0.9% U.S. Pharmacopeia (USP) or or 5% dextrose injection, USP.

In embodiments in which the patient is transitioning from administration of cangrelor during PCI to administration of cangrelor in preparation for surgery, the discontinuation of the administration of the PCI dosing regimen may occur at any time during the PCI continuous infusion. The administration of the bridge dosing regimen may occur as quickly as possible following the discontinuation of the administration of the PCI dosing regimen. In some embodiments, the discontinuation of the administration of the PCI dosing regimen and the administration of the bridge dosing regimen may be achieved simultaneously by lowering the PCI continuous infusion rate to the bridge continuous infusion rate. The administration of the bridge dosing regimen may be discontinued at least about one hour prior to administration of anesthesia for the surgery. Moreover, the administration of the bridge dosing regimen may be discontinued after no longer than about 7 days from initiation.

In embodiments in which the patient is transitioning from administration of cangrelor in preparation of surgery to administration of cangrelor during PCI, the discontinuation of the administration of the bridge dosing regimen can occur any time during the bridge continuous infusion. The administration of the PCI dosing regimen may occur as quickly as possible following the discontinuation of the administration of the bridge dosing regimen. In some embodiments, the discontinuation of the administration of the bridge dosing regimen and the administration of the PCI dosing regimen may be achieved simultaneously by increasing the bridge continuous infusion rate to the PCI continuous infusion rate. If the PCI dosing regimen includes the administration of a bolus, then the bolus can be administered immediately before or after the increase to the PCI continuous infusion rate. The administration of the continuous infusion of cangrelor in PCI dosing regimen may continue for the longer of (a) at least two hours, or (b) the duration of PCI. The continuous infusion may be continued for a total duration of about four hours.

EXAMPLES

Example 1

Figure 2:
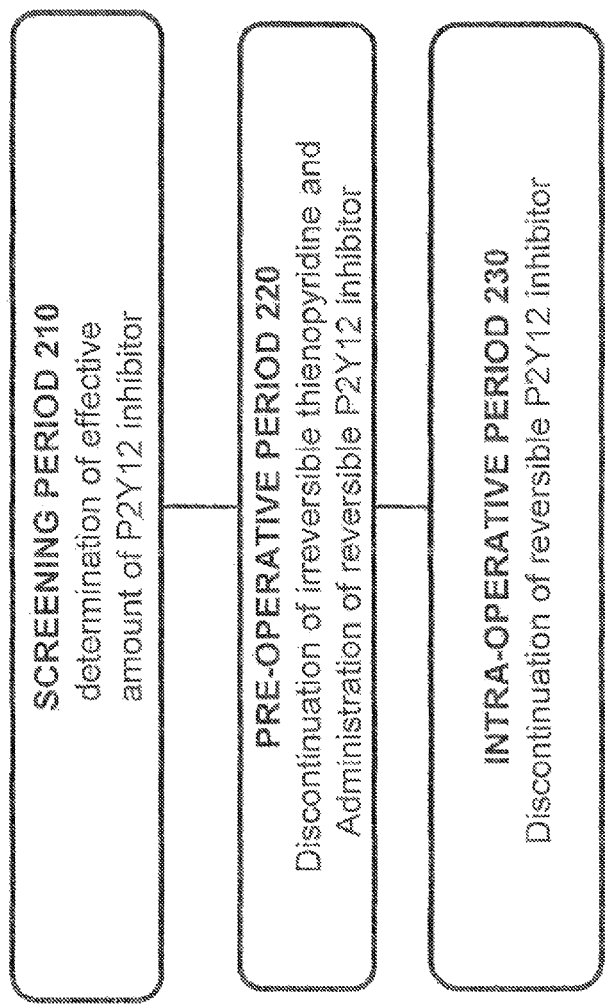
FIG. 2 is a flow chart of the time periods through which the present invention is performed.

Without limitations, FIG. 2 provides a brief summary as to how the methods described in the present invention may be used in a patient in need thereof. It should be understood that the method of the present invention is not limited to the procedure described in FIG. 2.

FIG. 2, shows a screening period 210 used for determining the dosage necessary for achieving platelet inhibition greater than a pre-determined level, for example, of approximately 60%. A pre-operative period 220 of up to approximately 7 days prior to surgery can be used for administration of a reversible, short-acting P2Y$_{12}$ inhibitor. An intra-operative period 230 lasting from the discontinuation of the reversible, short-acting P2Y$_{12}$ inhibitor to the end of surgery can be used.

During the screening period 210, the dosage of a reversible, short-acting P2Y$_{12}$ inhibitor, necessary to achieve platelet inhibition greater than approximately 60% can be determined. Other suitable levels of percent inhibition are approximately 65, 70, 75, 80, 85, 90, 95 and 100%. For example, intravenous infusion of a reversible, short-acting P2Y$_{12}$ inhibitor can be administered to a patient in doses typically ranging from about 0.5 μg/kg/min to about 5.0 μg/kg/min, preferably about 0.5 μg/kg/min to about 2.0 μg/kg/min and particularly at doses of 0.5 μg/kg/min, 0.75 μg/kg/min, 1.0 μg/kg/min, 1.5 μg/kg/min and 2.0 μg/kg/min, until measured platelet inhibition is greater than the pre-determined level. Smaller or larger doses may also be used as needed to achieve the required level of platelet inhibition.

Optionally, the dosage of a reversible, short-acting P2Y$_{12}$ inhibitor for any particular patient can also be determined ahead of time, so as to reduce the need to give multiple doses to achieve the required level of platelet inhibition. In all instances where measurement of platelet inhibition is needed, a baseline value should be obtained to accurately determine when acceptable levels have been reached.

During pre-operative period 220, administration of a reversible, short-acting P2Y$_{12}$ inhibitor can be initiated the day the decision is made to discontinue the long-acting irreversible platelet inhibitor and may be continued throughout pre-operative period 220. In another embodiment, administration of cangrelor can be made within 3 days of ceasing administration of the long-acting irreversible platelet inhibitor.

A patient can undergo CABG within 3 days of ceasing administration of the long-acting irreversible platelet inhibitor. The dose of such a reversible, short-acting P2Y$_{12}$ inhibitor can remain constant or can be periodic during the treatment period. Preferably the dosage of cangrelor remains continuous during the treatment period of about 2 to about 7 days. Treatment with reversible, short-acting P2Y$_{12}$ inhibitor may then be terminated from about one hour to about 6 hours before an invasive procedure.

Also during pre-operative period 220, any number of procedures and/or tests can be performed in conjunction with the present invention, such as hemoglobin, hematocrit, white blood cells, and platelet count testing; serum creatinine testing; measurement of inhibition of platelet activation; and assessment of concomitant medications, adverse events, serious adverse events and other various clinical endpoints. Additionally, procedures such as creatine kinase (CK) and creatine kinase with muscle- and brain-type subunits (CK-MB) and VerifyNow® P2Y12 assays, for example, can be performed within 24 hours prior to surgery.

During intra-operative period 230, administration of a reversible, short-acting P2Y$_{12}$ inhibitor can be stopped between from about at least 1 hour and up to approximately 3 hours prior to administration of anesthesia for surgery. Basic standard of care treatment is used for the surgical period as understood by those having skill in the art. Collection of concomitant medications and assessments of adverse events, serious adverse events and clinical endpoints can also be performed during this period as needed.

Example 2

FIG. 3 describes a non-limiting exemplary method for maintaining or reducing platelet activity in patients who were previously treated with thienopyridine prior to undergoing an invasive procedure such as CABG.

In FIG. 3, a total of 207 patients were studied. Patients were included in this study if they met all of the following criteria: (1) Must be at least 18 years of age; (2) Anticipate non-emergent CABG surgery, either "on-pump" or "off-pump," no sooner than 48 hours from randomization but no longer than 7 days from randomization, with patient to remain hospitalized until planned CABG; and (3) Have received a thienopyridine (at least 75 mg of clopidogrel, 500 mg ticlopidine, or 10 mg prasugrel) within 72 hours prior to enrollment in the study for either the treatment of an acute coronary syndrome, regardless of time from ACS, and/or as long-term preventative therapy following drug-eluting or bare metal stent treatment.

Patients were excluded from the study if any of the following exclusion criteria applied prior to randomization: (1) Confirmed or suspected pregnancy (if woman of child-bearing potential) or lactating females; (2) Cerebrovascular accident within one year; (3) Intracranial neoplasm or history of intracranial surgery; (4) History of bleeding diathesis; (5) Thrombocytopenia (platelet count of less than 100,000/µL; (6) Known International Normalized Ratio (INR) greater than 1.5 at screening; (7) Requirement for dialysis treatment (hemodialysis or peritoneal); (8) Estimated Glomeular filtration rate eGFR<30 ml/min; (9) Administration of abciximab within 24 hours of randomization or administration of eptifibitide or tirofiban within 12 hours of randomization; (10) Plans to continue oral anticoagulant, thienopyridine or GPIIb/IIIa antagonist therapy in the pre-operative period; (11) Known or suspected coagulopathy; (12) Refusal to receive blood transfusion; (13) Receipt of fibrinolytic therapy in the 12 hours preceding randomization; (14) Allergy, hypersensitivity, or contraindication to cangrelor, mannitol, sorbitol, or microcrystalline cellulose; (15) High likelihood of being unavailable for follow-up; (16) Participation in other studies involving the evaluation of other investigational drugs or devices within 30 days of randomization; or (17) Any disease or condition which, in the judgment of the health care provider, would place the patient at undue risk by participating in the study.

Patients were randomized into two groups, a cangrelor plus standard of care (SOC) group, and a placebo plus SOC group. A dose study was performed, for cangrelor plus SOC and placebo plus SOC respectively. A dose of 0.75 µg/kg/min was confirmed for the cangrelor plus SOC and placebo plus SOC groups.

In the placebo plus SOC group, patients received only SOC, in which the thienopyridine is discontinued after the need for surgery had been determined and a placebo infusion is administered. In the cangrelor plus SOC group, a cangrelor infusion was started in addition to SOC when the thienopyridine was discontinued after the need for surgery had been determined. The infusions (cangrelor or matching placebo) were continued throughout the pre-operative period. Patients can wait 5 days after discontinuation of clopidogrel before undergoing surgery but the timing of surgery can vary and be left to the discretion of the health care practitioner with a maximum of 7 days of cangrelor infusion.

Daily measurements of platelet inhibition were taken using the VerifyNow® P2Y12 assay system.

All patients randomized receive SOC and waited up to five days after discontinuation of thienopyridine before undergoing CABG. Antiplatelet therapy with aspirin was maintained during this time. Anti-thrombotics such as unfractionated heparin and enoxaparin were allowed and given at the discretion of the health care provider. It was recommended that enoxaparin be discontinued>24 hours before CABG although concomitant use of other antiplatelet and antithrombic agents is contemplated by the invention described here. It was recognized that clinical events may occur leading to surgery before the 5 day waiting period is completed and therefore the decision to proceed to surgery was left to the discretion of the health care provider.

For patients randomized to the cangrelor arm, cangrelor infusion was started as quickly as possible and no more than 6 hours after randomization. Patients received an infusion of cangrelor, in addition to their SOC therapy, at a rate of 0.75 µg/kg/min.

Cangrelor was infused continuously via a dedicated peripheral or central line for at least about 2 days and up to about 7 days. The dose of cangrelor remained constant during the infusion period. The cangrelor infusion was terminated at least one and no more than six hours before induction of anesthesia for the scheduled CABG surgery. Induction of anesthesia is defined as the start time of IV anesthesia. Patients were infused with cangrelor for a minimum of 48 hours prior to termination.

Patients not randomized to receive cangrelor received a placebo infusion administered in the same manner as the cangrelor infusion in addition to their SOC therapy.

FIGS. 4-1 and 4-2 include a table that summarizes the study assessments by time point. This study consisted of 5 periods: (1) Screening/Randomization Period, (2) Pre-operative (Days 1-7 defined as the period from randomization to discontinuation of cangrelor), (3) Intra-operative (from discontinuation of cangrelor to end of CABG surgery), (4) Postoperative Follow-up (from end of CABG surgery to hospital discharge), and (5) 30-Day Follow-up (30+5 days from time of CABG).

Pre-operative Period (Randomization until discontinuation of cangrelor): Just prior to the administration of cangrelor, a VerifyNow® P2Y12 Assay was performed to obtain a baseline assessment. Testing was performed irrespective of the timing of last dose of thienopyridine received. Immediately following the VerifyNow® P2Y12 Assay, the cangrelor composition was prepared and an infusion at the rate of 0.75 µg/kg/min was started. This infusion was maintained until 1 to 6 hours prior to anesthesia administration for the CABG surgery. The following tests were performed daily, at approximately the same time, during all days of cangrelor infusion: Hematology labs [hemoglobin, hematocrit, white blood cells (WBC), and platelet count] PRU and percent platelet inhibition determined by VerifyNow® P2Y12 Assay Assessment of concomitant medications. Within 12 hours prior to surgery, the following procedures were conducted: Additional VerifyNow® P2Y12 assay just prior to cangrelor termination. If the last on-infusion VerifyNow® sample was within 12 hours of cangrelor discontinuation, an additional draw was not required prior to termination of cangrelor.

Table 1 below represents the results of cangrelor and placebo treatment during the pre-operative period.

TABLE 1

Summary of PRU by Day

| | Stat | Cangrelor (N = 93) | Placebo (N = 90) |
|---|---|---|---|
| Screening: | | | |
| Patients w/PRU <240 PRU | n/N (%) | 53/85 (62.4) | 45/86 (52.3) |
| | N | 85 | 86 |
| | MEAN ± SD | 210.9 ± 94.0 | 214.1 ± 85.9 |
| | MEDIAN | 201.0 | 233.5 |
| | (Q1, Q3) | 166, 280 | 151, 279 |
| | (MIN, MAX) | 3, 418 | 10, 395 |
| Day 1 sample | | | |
| Patients w/PRU <240 PRU | n/N (%) | 80/80 (100) | 34/76 (44.7) |
| | N | 80 | 76 |
| | MEAN ± SD | 45.5 ± 47.1 | 232.7 ± 74.2 |
| | MEDIAN | 31.0 | 249.0 |
| | (Q1, Q3) | 5, 78 | 178, 287 |
| | (MIN, MAX) | 0, 169 | 47, 367 |
| Day 2 sample: | | | |
| Patients w/PRU <240 PRU | n/N (%) | 69/70 (98.6) | 25/73 (34.2) |
| | N | 70 | 73 |
| | MEAN ± SD | 58.8 ± 58.1 | 239.2 ± 71.1 |
| | MEDIAN | 40.0 | 256.0 |
| | (Q1, Q3) | 6, 100 | 218, 282 |
| | (MIN, MAX) | 0, 271 | 64, 354 |
| Day 3 sample: | | | |
| Patients w/PRU <240 PRU | n/N (%) | 55/55 (100) | 21/57 (36.8) |
| | N | 55 | 57 |
| | MEAN ± SD | 69.2 ± 59.8 | 250.4 ± 64.7 |
| | MEDIAN | 52.0 | 263.0 |
| | (Q1, Q3) | 8, 117 | 200, 306 |
| | (MIN, MAX) | 0, 229 | 105, 358 |
| Day 4 sample: | | | |
| Patients w/PRU <240 PRU | n/N (%) | 33/33 (100) | 7/34 (20.6) |
| | N | 33 | 34 |
| | MEAN ± SD | 80.3 ± 61.7 | 286.5 ± 65.5 |
| | MEDIAN | 78.0 | 296.0 |
| | (Q1, Q3) | 33, 115 | 241, 344 |
| | (MIN, MAX) | 1, 219 | 118, 406 |
| Day 5 sample: | | | |
| Patients w/PRU <240 PRU | n/N (%) | 7/7 (100) | 6/24 (25.0) |
| | N | 7 | 24 |
| | MEAN ± SD | 52.1 ± 58.1 | 284.0 ± 64.0 |
| | MEDIAN | 30.0 | 285.5 |
| | (Q1, Q3) | 9, 117 | 244, 328 |
| | (MIN, MAX) | 7, 151 | 140, 388 |
| Day 6 sample: | | | |
| Patients w/PRU <240 PRU | n/N (%) | 6/6 (100) | 3/14 (21.4) |
| | N | 6 | 14 |
| | MEAN ± SD | 62.7 ± 74.7 | 291.3 ± 54.1 |
| | MEDIAN | 45.5 | 280.0 |
| | (Q1, Q3) | 9, 67 | 250, 329 |
| | (MIN, MAX) | 3, 206 | 217, 399 |
| Day 7 sample: | | | |
| Patients w/PRU <240 PRU | n/N (%) | 1/1 (100) | 0/2 (0.0) |
| | N | 1 | 2 |
| | MEAN ± SD | 3.0 ± . | 343.5 ± 4.9 |
| | MEDIAN | 3.0 | 343.5 |
| | (Q1, Q3) | 3, 3 | 340, 347 |
| | (MIN, MAX) | 3, 3 | 340, 347 |
| Last on-treatment sample: | | | |
| Patients w/PRU <240 PRU | n/N (%) | 83/84 (98.8) | 26/84 (31.0) |
| | N | 84 | 84 |
| | MEAN ± SD | 68.9 ± 67.8 | 263.7 ± 68.3 |
| | MEDIAN | 53.0 | 263.5 |
| | (Q1, Q3) | 8, 110 | 227, 311 |
| | (MIN, MAX) | 0, 271 | 81, 399 |
| Last post-treatment pre-CABG: | | | |
| Patients w/PRU <240 PRU | n/N (%) | 21/78 (26.9) | 15/75 (20.0) |
| | N | 78 | 75 |
| | MEAN ± SD | 279.7 ± 106.5 | 297.8 ± 67.3 |
| | MEDIAN | 293.0 | 299.0 |
| | (Q1, Q3) | 228, 357 | 256, 345 |
| | (MIN, MAX) | 1, 471 | 144, 445 |

The data in Table 1 indicates that infusion of Cangrelor at a dose of 0.75 μg/kg/min between day 1 to day 7 maintains PRU values below 240 in over 90% of the patients studied. The table further indicates that for the "last post-treatment pre-CABG" where cangrelor infusion is terminated but prior to CABG, the level of PRU has resumed to levels prior to cangrelor treatment.

Intra-operative Period (Period from discontinuation of cangrelor until end of CABG surgery): The Intra-operative period started at termination of cangrelor infusion (surgery start is defined as time of first incision). Cangrelor infusion was stopped at least 1 hour and a maximum of 6 hours prior to administration of anesthesia for surgery. Standard of care treatment was used for the surgical period. Collection of the following assessments were conducted during this period: (i) serum creatinine and liver function tests (LFTs)—following discontinuation of cangrelor but prior to surgery (surgery start time is defined as the time of first surgical incision); (ii) VerifyNow® P2Y12 assay just prior to first surgical incision; and (iii) concomitant medications and assessments of adverse events, serious adverse events and clinical endpoints.

In the case of administering and ceasing the therapy prior to surgery in accordance with one embodiment of the present invention, such use allows patients to undergo surgery or other invasive procedures without excessive perioperative bleeding.

Table 2 represents the bleeding risks associated with cangrelor and placebo treatment.

TABLE 2

Summary of CABG Related Bleeding During the CABP Procedure through Hospital Discharge

| | Stat | Cangrelor (N = 106) | Placebo (N = 101) |
|---|---|---|---|
| CABG related bleeding | n/N (%) | 10/102 (9.8) | 10/96 (10.4) |
| Fatal bleeding | n/N (%) | 0 | 0 |
| Periop. intracranial bleeding | n/N (%) | 0 | 0 |
| Re operation for bleeding | n/N (%) | 2/102 (2.0) | 2/96 (2.1) |
| Whole Blood or pRBC Transfusion >=5 units | n/N (%) | 7/102 (6.9) | 8/96 (8.3) |
| 24 hour CT output >=2 L | n/N (%) | 3/102 (2.9) | 4/96 (4.2) |

The results of Table 2 indicates that bleeding risk associated with cangrelor treatment is the same as or similar to treatment with placebo.

Table 3 represents the overall incidence of ischemic events

TABLE 3

Overall Incidence of Ischemic Events

|  | Stat | Cangrelor (N = 106) | Placebo (N = 101) |
|---|---|---|---|
| Pre-procedure | | | |
| Death/MI/IDR/Stroke | n/N (%) | 3/106 (2.8) | 4/101 (4.0) |
| Death | n/N (%) | 1/106 (0.9) | 3/101 (3.0) |
| MI | n/N (%) | 2/106 (1.9) | 0/101 (0.0) |
| IDR | n/N (%) | 1/106 (0.9) | 0/101 (0.0) |
| Stroke | n/N (%) | 0/106 (0.0) | 1/101 (1.0) |
| Post-procedure | | | |
| Death/MI/IDR/Stroke | n/N (%) | 4/102 (3.9) | 4/96 (4.2) |
| Death | n/N (%) | 1/102 (1.0) | 2/96 (2.1) |
| MI | n/N (%) | 2/102 (2.0) | 1/96 (1.0) |
| IDR | n/N (%) | 2/102 (2.0) | 0/96 (0.0) |
| Stroke | n/N (%) | 1/102 (1.0) | 1/96 (1.0) |
| Pre and Post-procedures | | | |
| Death/MI/IDR/Stroke | n/N (%) | 10/106 (9.4) | 8/101 (7.9) |
| Death | n/N (%) | 2/106 (1.9) | 5/101 (5.0) |
| MI | n/N (%) | 4/106 (3.8) | 1/101 (1.0) |
| IDR | n/N (%) | 6/106 (5.7) | 0/101 (0.0) |
| Stroke | n/N (%) | 1/106 (0.9) | 2/101 (2.0) |

The results of Table 3 indicate that the ischemic events relating to the methods described herein with the use of cangrelor are comparable to the placebo.

Post-operative Period (Period from end of CABG surgery to hospital discharge): The following procedures were performed following surgery (end of CABG surgery is defined as the placement of the last suture): VerifyNow® P2Y12 Assay was performed within 1 hour following surgery Hematology labs, 12 lead-ECG and VerifyNow® P2Y12 Assay were performed 24-hours (±1 h) following surgery. Chest tube output will be assessed at 4 hours (±1 h) and 24 hours (±1 h) following surgery.

Example 3

In another example and in accordance with one embodiment of the present invention, the administration of the at least one reversible, short-acting $P2Y_{12}$ inhibitor occurs during an invasive procedure being performed on the subject. In this manner, it is contemplated that the administration of the inhibitor would occur intravenously as the subject cannot take the therapy orally.

Example 4a

In another example and in accordance with another embodiment of the present invention, the administration of the at least one reversible, short-acting $P2Y_{12}$ inhibitor occurs after an invasive procedure has been performed on the subject. The administration of the inhibitor in the post surgery scenario can occur in a variety of methods as described above. It is contemplated that the administration of the inhibitor may also occur intravenously post surgery if the subject cannot take the therapy orally, for example, if the subject is comatose.

Example 4b

The study for using cangrelor in early post-operative period:

Current standard of care for antiplatelet maintenance therapy after PCI in patients with implanted stents is based on recommendations of the ACC/AHA guidelines (Fleisher LA, et al., ACC/AHA 2007 guidelines on perioperative cardiovascular evaluation and care for noncardiac surgery: a report of the ACC/AHA Task Force on Practice Guidelines. Circulation. 2007 Oct. 23; 116(17): e418-99) that suggest an early initiation of dual antiplatelet therapy and continuation of maintenance therapy with aspirin and clopidogrel after PCI from 6 to 12 months, depending on the stent type, in order to prevent post-procedural stent thrombosis. Both aspirin and clopidogrel are irreversible platelet antagonists, therefore ACC/AHA guidelines recommend cessation of clopidogrel before non-emergent surgical procedures in order to minimize bleeding risks.

However, should patients with implanted stents require a surgical procedure, early cessation of clopidogrel would increase the risk for ischemic events and stent thrombosis (Berger et al., Circulation. 2002 Oct. 22; 106(17): 2284-7; Ho et al. JAMA. 2008 Feb. 6; 299(5): 532-9). Conversely, maintaining irreversible platelet inhibition with aspirin and clopidogrel leads to unacceptable operative bleeding risk (Fox et al., Circulation. 2004; 110: 1202-1208; Shim et al., J Thorac Cardiovasc Surg. 2007 July; 134(1): 59-64; Pickard et al., Pharmacotherapy. 2008 March; 28(3): 376-92. Review).

Because of the risk of bleeding from the surgical sites, surgeons prefer to avoid using anticoagulant agents in early post-operative period especially with irreversible oral therapy that will not allow predicting the level of platelet inhibition and fast recovery of platelet function when surgical procedure could be associated with high risk of post-operative bleeding.

It is well known that surgical interventions trigger platelet activation and aggregation, hence increasing the risk of stent thrombosis in post-operative period if patient do not continue antiplatelet therapy.

It has been demonstrated in several studies that early initiation of anticoagulant therapy may diminish the risk of venous thrombosis (Segers A. J Thromb Haemost. 2008 August; 6(8): 1313-8; Turpie et al., Lancet. 2009 May 1), however there is no consensus or standard antiplatelet therapy regimen designed to reduce the risk of arterial stent thrombosis in patients with implanted stents requiring surgical procedures.

Typically, at conclusion of surgical procedure a complete hemostasis is achieved, however, the risk of bleeding from the surgical site remains high during the first post-operative hours. Initiation of antiplatelet therapy during the immediate-early period after surgery may further increase that risk. Conversely, a delay of continuation of antiplatelet maintenance therapy will significantly increase the risk of stent thrombosis, considering that surgical procedure triggers platelet activation and aggregation. Therefore, an early therapy with reversible antiplatelet agent that could be titrated to a desirable level of platelet inhibition and have ultra-short platelet function recovery time could be beneficial in preventing stent thrombosis in that category of patients. Moreover, this type of agent will be safe because it may allow complete recovery of platelet function after discontinuation in case of bleeding.

Cangrelor is a potent, reversible and specific $P2Y_{12}$ receptor antagonist that would allow overcoming the limitations of currently used dual antiplatelet therapy with aspirin and clopidogrel thanks to its rapid onset and offset of action with steady-state plasma concentrations that can be achieved within minutes and titrated to modulate the level of platelet inhibition and most importantly, it is rapidly metabolized with an short half-life, allowing complete recovery of platelet function in less than 60 min. Therefore, cangrelor could be an ideal antiplatelet agent for managing platelet inhibition in early post-operative period in patients with implanted stents requiring a surgical procedure.

The optimal platelet inhibitory dose and regimen for cangrelor infusion in post-operative period and transitioning to oral antiplatelet therapy can be determined.

The patient population can be ACS patients with implanted stents after PCI who require a major surgical procedure (CABG, gastrointestinal (GI) anastomoses, pulmonary resection, prostatectomy, orthopedic procedures, etc.), N=40 subjects (4 groups with 10 subjects in each group). Cangrelor infusion will be initiated 1-2 hours after completion of surgical procedure at surgeons' discretion. The subjects will be randomized into the following groups:

Group 1: Cangrelor 0.5 µg/kg/min dose infusion for 24 hrs transitioning to oral antiplatelet therapy with 300 mg of clopidogrel loading dose after infusion discontinuation followed by 75 mg daily maintenance dose thereafter;

Group 2: Cangrelor 0.5 µg/kg/min infusion for 24 hrs transitioning to oral antiplatelet therapy with 600 mg of clopidogrel loading dose after infusion discontinuation followed by 75 mg daily maintenance dose thereafter;

Group 3: Cangrelor 1 µg/kg/min infusion for 24 hrs transitioning to oral antiplatelet therapy after infusion discontinuation transitioning to oral antiplatelet therapy with 300 mg of clopidogrel loading dose after infusion discontinuation followed by 75 mg daily maintenance dose thereafter;

Group 4: Cangrelor 1 µg/kg/min infusion for 24 hrs transitioning to oral antiplatelet therapy after infusion discontinuation transitioning to oral antiplatelet therapy with 600 mg of clopidogrel loading dose after infusion discontinuation followed by 75 mg daily maintenance dose thereafter.

The primary endpoints will be: (1) acute sent thrombosis during the 48 hrs after the surgical procedure, and (2) major and minor bleedings during the 48 hrs after the surgical procedure.

The methods of evaluation will be: (1) platelet aggregation using VerifyNow® P2Y12 test, (2) hemodynamic measurements, (3) blood tests, (4) clinical observations for minor capillary bleeding signs (petechiae, hematoma), (5) Diagnostic imaging of intracranial, peritoneal and pleural cavities using computed tomography (CT), magnetic resonance imaging (MRI), ultrasound (US), when necessary to detect potential bleeding complications (blood accumulation).

Example 5

Population Pharmacodynamic Evaluation of Cangrelor

Objective: The objective of this evaluation was to develop a population pharmacodynamic model to describe the concentration effect relationship between cangrelor exposure and the marker of platelet aggregation, namely PRU, as measured by VerifyNow®, Accumetrics in order to, among other things, determine how best to transition from the bridge dose to the PCI dose, and vice versa.

Data and Database Creation: The database created for this evaluation included a total of 1102 PRU observations from 220 bridge and PCI patients. A summary of the demographics is provided in Table 4. These patients were generally older and heavier than volunteers.

TABLE 4

Summary of the Demographics of the Patients Involved in the Study.

| Covariate (units) | Mean | Median | SD | Max | Min |
|---|---|---|---|---|---|
| Age (yrs) | 63 | 62 | 11 | 92 | 36 |
| Weight (kg) | 86.8 | 85.4 | 16 | 154 | 52 |
| BMI (kg/m2) | 29.5 | 29.1 | 5.07 | 50.1 | 19.4 |

| Sex | Male | Female |
|---|---|---|
| Number | 161 | 59 |

| Study | CHAMPION PCI/Platform (PCI) Platelet Substudy | Bridge |
|---|---|---|
| Number | 104 | 116 |
| Patient type | PCI | ACS | Stent |
| Number | 54 | 69 | 97 |

| Treatment Group | PCI/substudy, 30 µg/kg bolus + 4 µg/kg/min infusion | Cohort 1: 0.5 µg/kg/min | Cohort 1: 0.75 µg/kg/min | Cohort 2: 0.75 µg/kg/min |
|---|---|---|---|---|
| Number | 104 | 5 | 6 | 105 |

ACS denotes acute coronary syndrome. PCI denotes percutaneous coronary intervention.

Simulation Assessments: In order to address the pharmacodynamic objectives and show how best to transition from one dose to the other dose (i.e., Bridge and PCI), stochastic simulation was performed in NONMEM®. A PRU value of 208 was chosen throughout the evaluation as the cutoff to evaluate the effectiveness of varying doses of cangrelor in different patient types. The results were evaluated graphically by generating 95% confidence intervals and by summarizing the percentage of patients expected to achieve a PRU value of 208 or less. For each simulation scenario, 1000 patients were simulated using covariates drawn from the original distribution of covariate values. Parameter precision was not taken into account for these simulations.

Patients from the bridge subset of data were sampled. At varying times after initiation of the bridge dose, the patient type was switched to the PCI type (to reflect reduced sensitivity to cangrelor) and the dose was increased to the PCI dose. The percentage of subjects achieving the desired PRU result of 208 or lower were tabulated. For completeness, the reverse transition (from PCI to bridge) was also simulated, and results tabulated.

Description of PRU Pharmacodynamic Model: The PRU pharmacodynamic model was a direct effect sigmoidal inhibitory model with terms describing the between subject variability included on the drug effect parameter (Emax) and baseline. An additive residual error was used. The model incorporated a slowly increasing baseline in bridge patients (attributable to the effect of previous dosing with clopidogrel wearing off) and a slowly decreasing baseline in PCI patients (owing to the thrombotic stimulus of the stenting/PCI gradually lessening after the procedure together with onset of effect of other post procedure treatments). The model also included a covariate for patient type on drug effect and the effects of age and sex on baseline. The equations for the final PRU pharmacodynamic model are provided below.

$$BaselinePRU = \theta_6 * (1 - sex * \theta_{11}) * \left(\frac{Age}{30}\right)^{\theta_{on}} * \exp(\eta 5)$$

-continued $$Eff = \theta_7 * (1 - \text{patient type} * \theta_{10}) * \exp(\eta 4)$$

$$IC50 = \theta_8$$

$$\gamma = \theta_9$$

if (Study − 1)$wearoff - \theta_{13}$ else $\theta_{14}$ $$DrugEffect = \frac{Eff * C p_T}{IC50^T + Cp^T}$$

$$PRU = BaselinePRU - DrugEffect - wearoff * \text{Time(hrs)}$$

The parameters were estimated with good precision with the exception of the age effect on baseline. All other diagnostics and model evaluations suggested that the model performance was acceptable. The parameters from the model are provided in Table 5.

TABLE 5

Parameter estimates for base PRU pharmacodynamic model.

| Parameter (Units) | Population Mean | SE (CV %) | Between Subject Variability | SE (CV %) |
|---|---|---|---|---|
| Baseline | 215 | 7 | 23.22 | 15 |
| Wear off PCI (1/h) | −3.15 | 13.7 | | |
| Wear off bridge (1/h) | 0.838 | 7.3 | | |
| Age effect | 0.228 | 39.7 | | |
| Gender effect | −0.162 | 25.3 | | |
| Drug Effect | 148 | 6.2 | 19.21 | 31.7 |
| PCI patient effect | −0.624 | 17 | | |
| IC50 | 0.0717 | 35.4 | NE | NE |
| Gamma | 1.71 | 21 | NE | NE |
| Additive Residual Error | 62.6 | | 2.7 | |

NE—not estimated.

Several covariates were identified in this evaluation. There was an effect of gender on the baseline PRU, with females having a 16% higher baseline PRU than males. Age was also found to be important on the baseline PRU value. The impact of age is provided in Table 6.

TABLE 6

Effect of age on baseline PRU.

| Age (yrs) | Baseline PRU | Percent of Reference |
|---|---|---|
| 30 | 215 | 100 |
| 40 | 230 | 107 |
| 50 | 242 | 112 |
| 60 | 252 | 117 |
| 70 | 261 | 121 |
| 80 | 269 | 125 |

Figure 5:
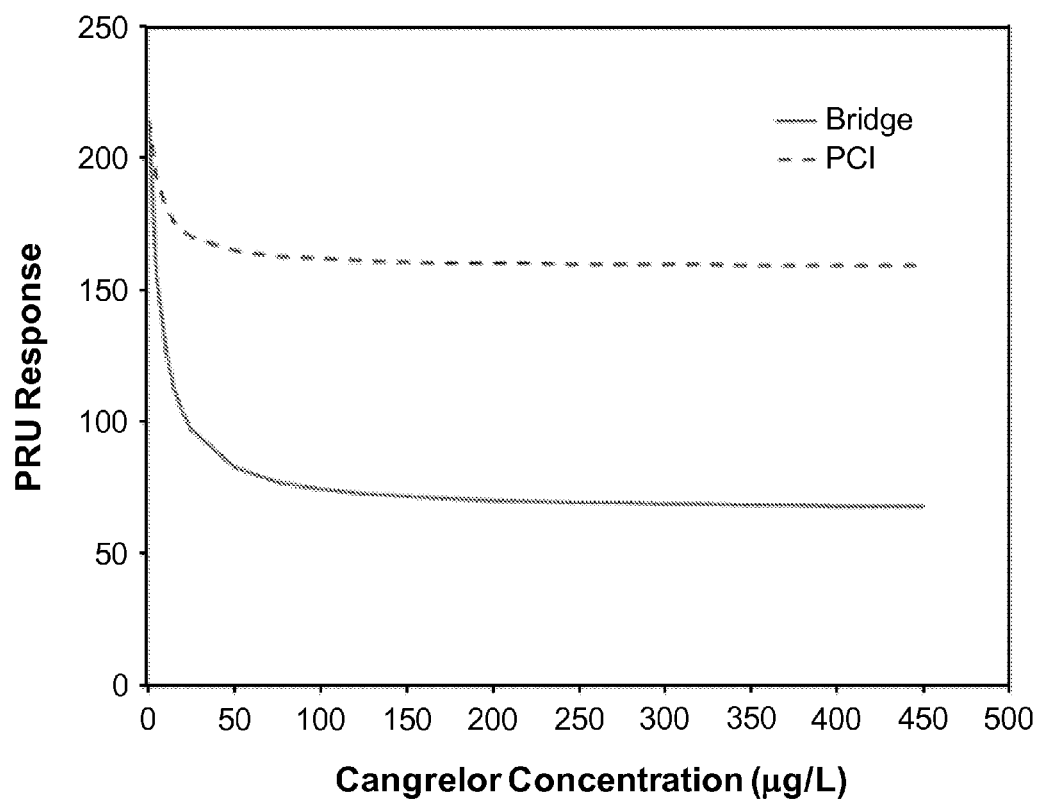
FIG. 5 shows a comparison of PRU responses versus cangrelor concentration for patients receiving a PCI dosing regimen and for patients receiving a bridge dosing regimen.

Over the age range from 30 to 80 years, the baseline PRU would be expected to increase by 25%. There was a larger impact of patient type (i.e., PCI patient versus bridge patient) on the drug effect which is shown in FIG. 5. This impact is a 62% decreased effect in PCI relative to bridge and shows why the percentage of simulated PCI patients achieving the threshold response of 208 is somewhat lower than seen in the bridge patients.

Simulation Results—Evaluation of the Probability of Achieving the Desired

PRU Cutoff: The probability of the PCI and bridge patients achieving the desired PRU cutoff value of 208 is provided for the overall indication in Table 7.

TABLE 7

Probability of achieving desired PRU result by patient type - overall findings.

| Study | Patient Type | Dose | Probability |
|---|---|---|---|
| 1 | PCI | 30 μg/kg bolus with 4 μg/kg/min | 0.827462 |
| 2 | Bridge | 0.75 μg/kg/min | 0.961949 |

As can be seen, despite the lower dose used for the bridge patients, the probability of achieving the threshold is higher in these patients than the PCI patients because the PCI patients had a higher immediate thrombotic stimulus.

Similarly the probability of maintaining the PRU below the threshold after stratification of patients by weight over the range of weights in the database showed no overall trends (Table 8), suggesting that the drug concentration is sufficient to provide approximately 80% at or below threshold for PCI patients and over 90% at or below threshold PRU for bridge patients with the suggested dose.

TABLE 8

Probability of achieving desired PRU result by patient type and weight.

| Study | Patient Type | Dose | Weight Range (kg) | Probability |
|---|---|---|---|---|
| 1 | PCI | 30 μg/kg bolus with 4 μg/kg/min | (50, 80) | 0.839885 |
| 1 | PCI | 30 μg/kg bolus with 4 μg/kg/min | (80, 90) | 0.795222 |
| 1 | PCI | 30 μg/kg bolus with 4 μg/kg/min | (90, 100) | 0.7975 |
| 1 | PCI | 30 μg/kg bolus with 4 μg/kg/min | (100, 120) | 0.87275 |
| 1 | PCI | 30 μg/kg bolus with 4 μg/kg/min | (120, 160) | 0.856 |
| 2 | Bridge | 0.75 μg/kg/min | (50, 80) | 0.95797 |
| 2 | Bridge | 0.75 μg/kg/min | (80, 90) | 0.98004 |
| 2 | Bridge | 0.75 μg/kg/min | (90, 100) | 0.952081 |
| 2 | Bridge | 0.75 μg/kg/min | (100, 120) | 0.957313 |
| 2 | Bridge | 0.75 μg/kg/min | (120, 160) | 0.9915 |

There was no marked trend in the probability of patients achieving the threshold with age (Table 9).

TABLE 9

Probability of achieving desired PRU result by patient type and age.

| Study | Patient Type | Dose | Age Range (yrs) | Probability |
|---|---|---|---|---|
| 1 | PCI | 30 μg/kg bolus with 4 μg/kg/min | (30, 50) | 0.896722 |
| 1 | PCI | 30 μg/kg bolus with 4 μg/kg/min | (50, 60) | 0.806719 |
| 1 | PCI | 30 μg/kg bolus with 4 μg/kg/min | (60, 70) | 0.836735 |
| 1 | PCI | 30 μg/kg bolus with 4 μg/kg/min | (70, 80) | 0.778786 |
| 1 | PCI | 30 μg/kg bolus with 4 μg/kg/min | (80, 100) | 0.791333 |
| 2 | Bridge | 0.75 μg/kg/min | (30, 50) | 0.994444 |
| 2 | Bridge | 0.75 μg/kg/min | (50, 60) | 0.98919 |
| 2 | Bridge | 0.75 μg/kg/min | (60, 70) | 0.984217 |
| 2 | Bridge | 0.75 μg/kg/min | (70, 80) | 0.93135 |
| 2 | Bridge | 0.75 μg/kg/min | (80, 100) | 0.869444 |

There was no marked trend in the probability of patients achieving the threshold with gender (Table 10).

TABLE 10

Probability of achieving desired PRU result by patient type and sex.

| Study | Patient Type | Dose | Sex | probability |
|---|---|---|---|---|
| 1 | PCI | 30 μg/kg bolus with 4 μg/kg/min | Male | 0.866044 |
| 1 | PCI | 30 μg/kg bolus with 4 μg/kg/min | Female | 0.754583 |
| 2 | Bridge | 0.75 μg/kg/min | Male | 0.982444 |
| 2 | Bridge | 0.75 μg/kg/min | Female | 0.901222 |

These results support the selection of a higher dose for PCI patients than for Bridge patients and suggest that there should be no need to adjust dose for age or gender.

Figure 6:
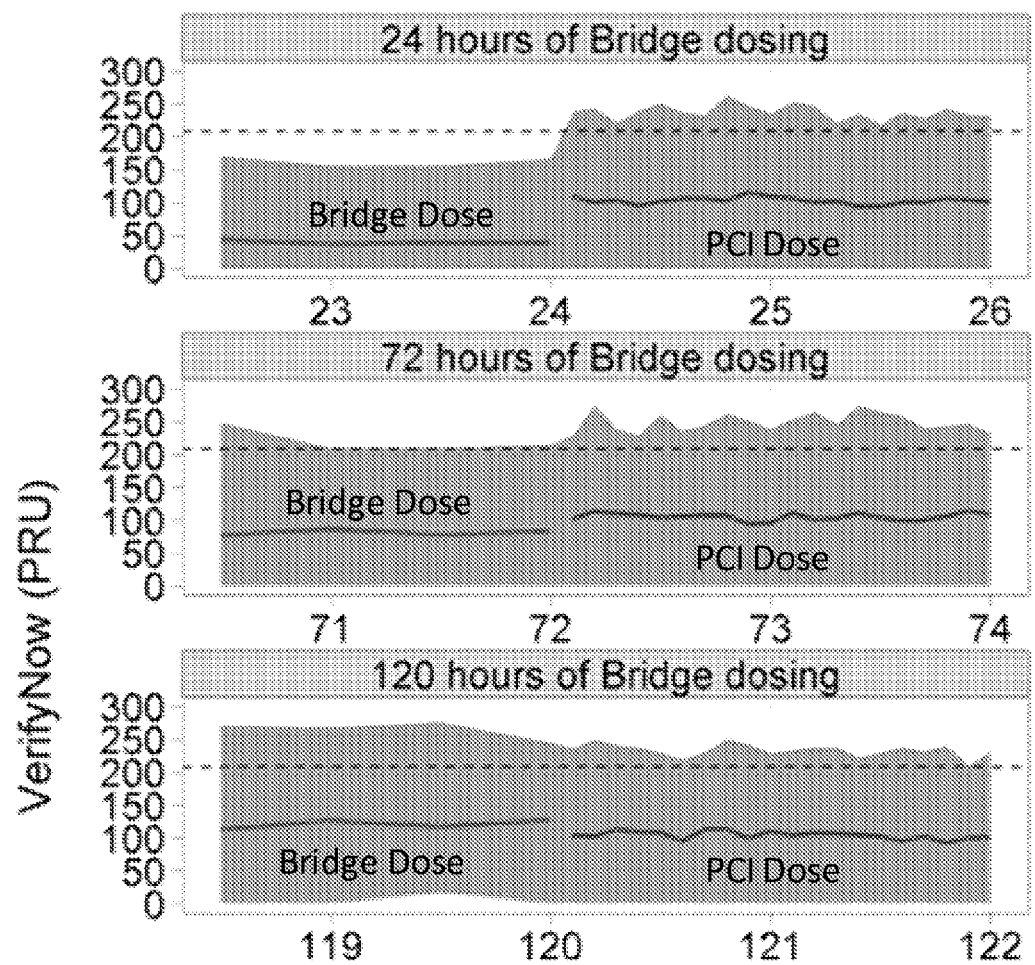
FIG. 6 shows a simulated range of PRU responses for a male patient, 62 years old and weighing 90 kg, with intravenous (IV) bolus loading dose for PCI, transitioning from the bridge dosing regimen to the PCI dosing regimen (the shaded areas are the confidence intervals about the lines and the dashed line is the cut-off PRU value of 208, associated high sensitivity and specificity for the presence of $P2Y_{12}$ inhibition)
Figure 7:
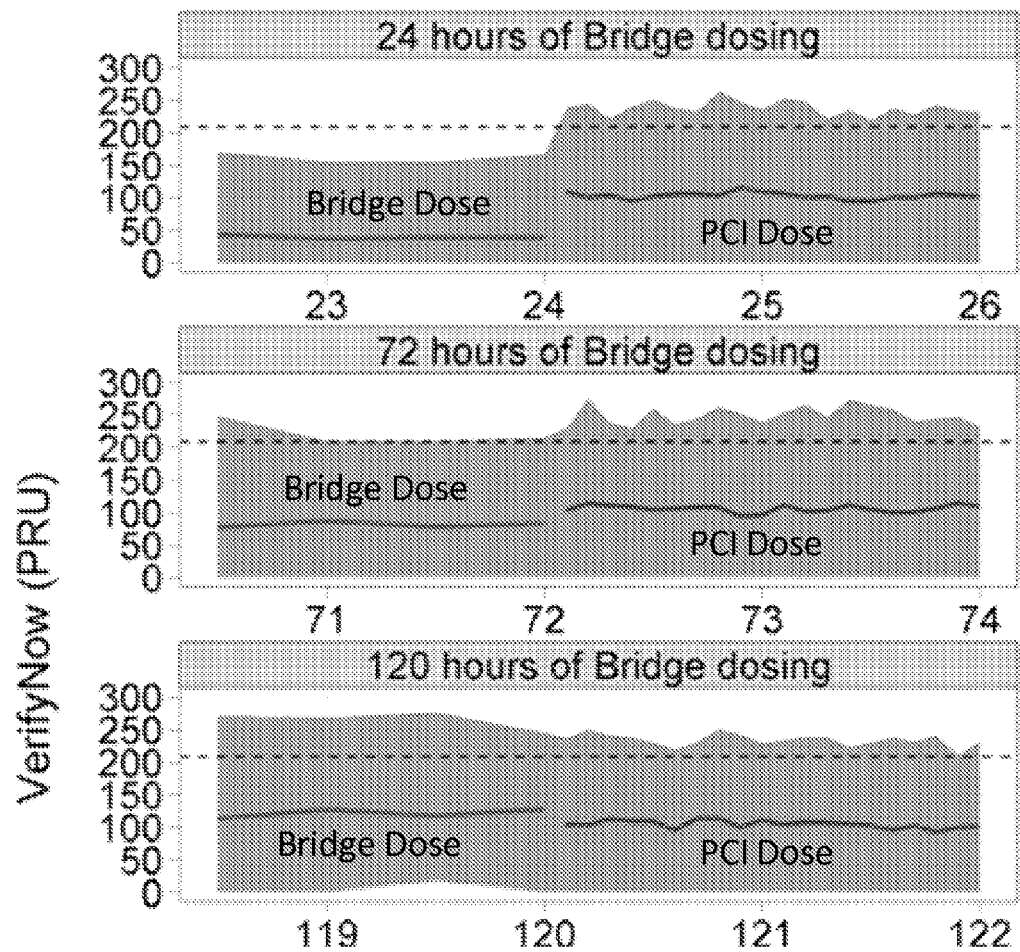
FIG. 7 shows a simulated range of PRU responses for a male patient, 62 years old and weighing 90 kg, with no IV bolus loading dose for PCI, transitioning from the bridge dosing regimen to the PCI dosing regimen (the shaded areas are the confidence intervals about the lines and the dashed line is the cut-off PRU value of 208, associated high sensitivity and specificity for the presence of $P2Y_{12}$ inhibition)
Figure 8:
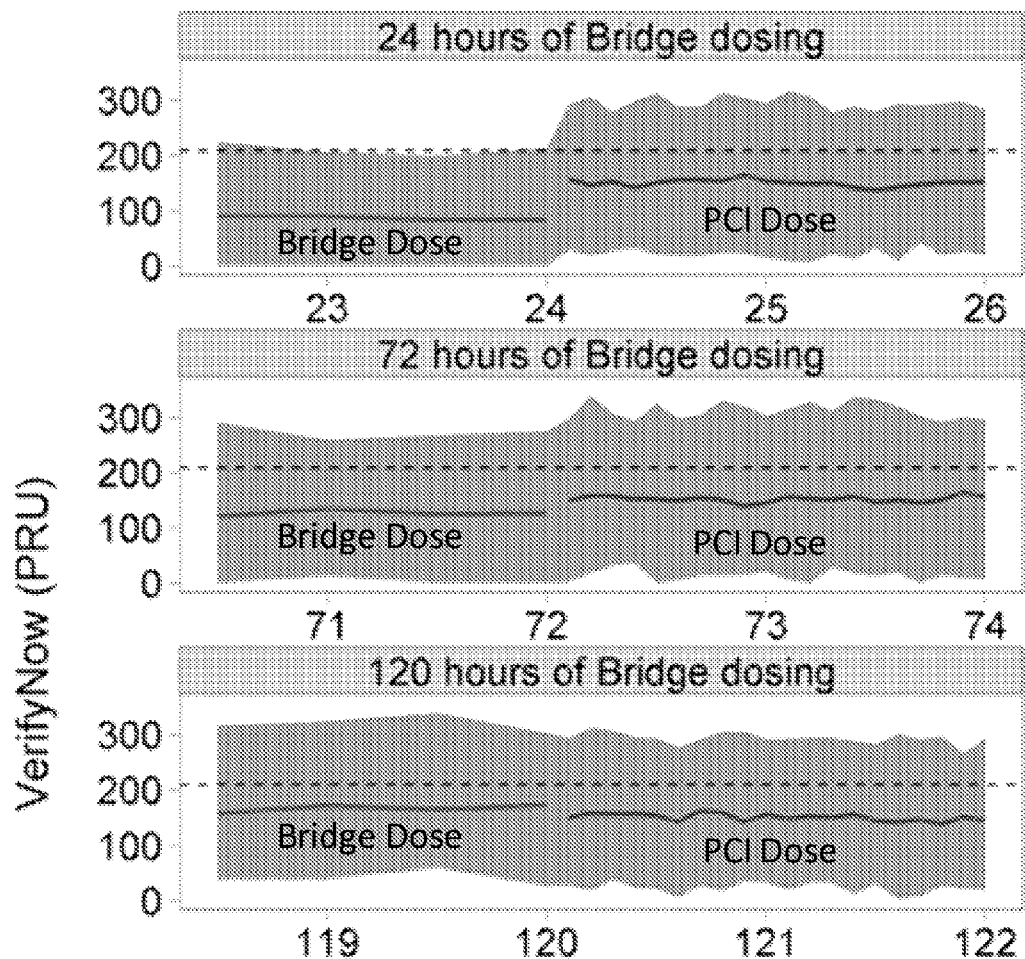
FIG. 8 shows a simulated range of PRU responses for a female patient, 66 years old and weighing 60 kg, with IV bolus loading dose for PCI, transitioning from the bridge dosing regimen to the PCI dosing regimen (the shaded areas are the confidence intervals about the lines and the dashed line is the cut-off PRU value of 208, associated high sensitivity and specificity for the presence of $P2Y_{12}$ inhibition)
Figure 9:
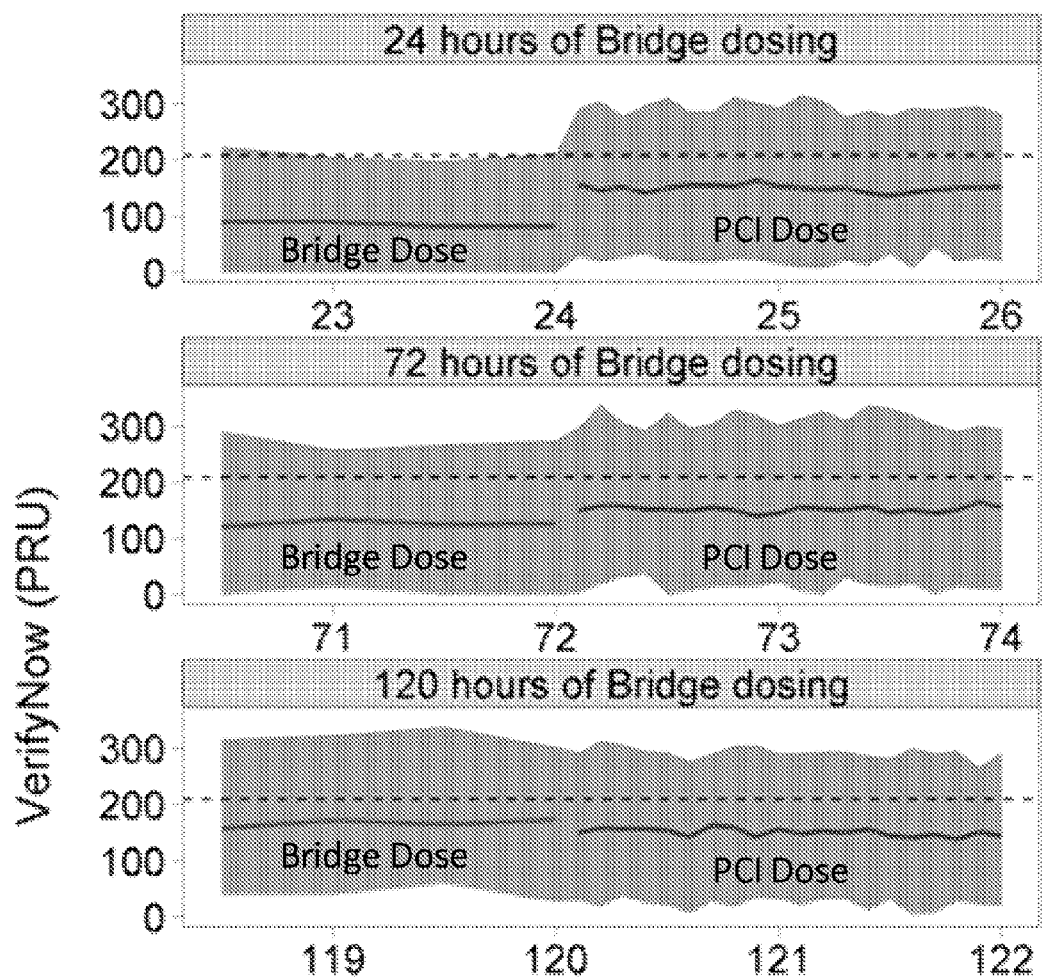
FIG. 9 shows a simulated range of PRU responses for a female patient, 66 years old and weighing 60 kg, with no IV bolus loading dose for PCI, transitioning from the bridge dosing regimen to the PCI dosing regimen (the shaded areas are the confidence intervals about the lines and the dashed line is the cut-off PRU value of 208, associated high sensitivity and specificity for the presence of $P2Y_{12}$ inhibition)

Transition from Bridge to PCI: The results of the simulated transition from the bridge setting (0.75 μg/kg/min) to the PCI setting (4 μg/kg/min) with and without the administration of an IV bolus loading dose for PCI (30 μg/kg) are provided for a reference male patient in FIG. 6 and FIG. 7, respectively. As was seen with the evaluation of probability of achieving the threshold PRU response, the probability is generally lower for the PCI than bridge patient in all settings. The same scenarios were simulated in a reference female patient with and without the IV bolus dose (FIG. 8 and FIG. 9, respectively). The benefit of adding a bolus dose when transitioning from bridge to PCI is somewhat limited, but the probability of maintaining the PRU value below 208 is higher with the recommended loading dose than without such IV bolus dose prior to PCI.

Figure 10:
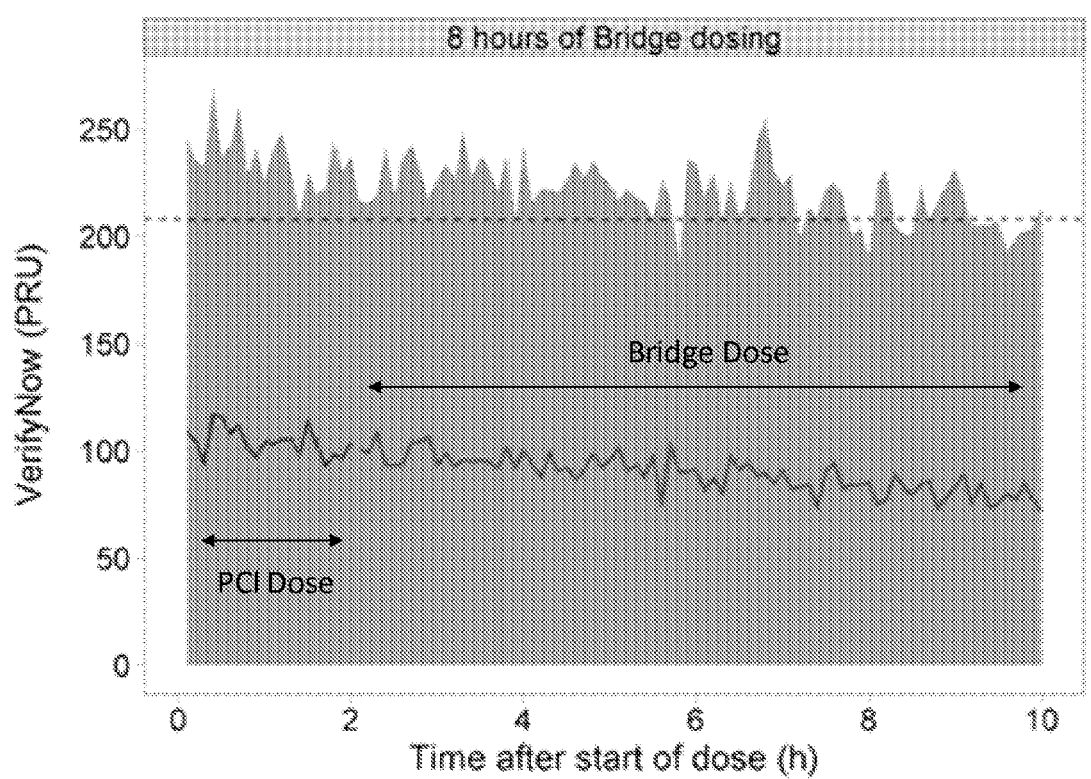
FIG. 10 shows a simulated range of PRU responses for male patient, 62 years old and weighing 90 kg, transitioning from the PCI dosing regimen to the bridge dosing regimen (the shaded areas are the confidence intervals about the lines and the dashed line is the cut-off PRU value of 208, associated high sensitivity and specificity for the presence of $P2Y_{12}$ inhibition)
Figure 11:
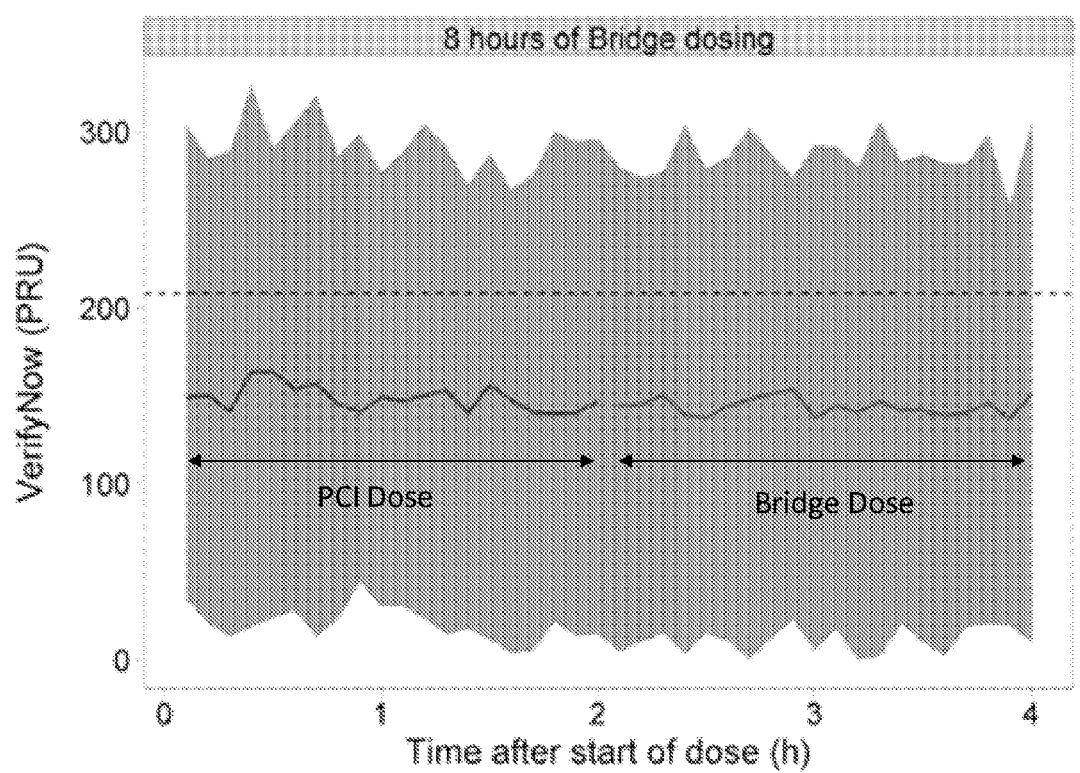
FIG. 11 shows a simulated range of PRU responses for female patient, 66 years old and weighing 60 kg, transitioning from the PCI dosing regimen to the bridge dosing regimen (the shaded areas are the confidence intervals about the lines and the dashed line is the cut-off PRU value of 208, associated high sensitivity and specificity for the presence of $P2Y_{12}$ inhibition).

Transition from PCI to Bridge: The results of the stochastic simulations from the PCI setting (30 μg/kg bolus with 4 μg/kg/min) to the bridge setting (0.75 μg/kg/min) are provided for the same virtual male and female patient in FIG. 10 and FIG. 11, respectively. In these simulations, patients received the recommended PCI dose for 2 hours, then were transitioned directly to the recommended bridge dose for 8 hours. PRU samples were taken hourly. Because these virtual patients were simulated to reflect a PCI patient (and who would not therefore have had a high dose of cangrelor prior to PCI), the wearing off effect seen with the bridge study was turned off. However the ability of a subject to respond to cangrelor was changed once bridge dosing was initiated.

Although these figures suggest a substantial difference between males and females, the determined probability of achieving a PRU below the threshold of 208 was similar. Thus these figures reflect the inherent variability of the PRU assay more than any difference in inherent responsiveness to treatment.

The results of the stochastic simulations suggest that when transitioning from the bridge setting to the PCI setting, or vice versa, there is no need to modify the cangrelor dosing (e.g., dose titration) from that which is routinely used for these indications. PCI patients being transitioned to surgery can be switched from 4 μg/kg/min cangrelor directly to 0.75 μg/kg/min cangrelor. Surgical patients being transitioned to PCI can be switched directly from 0.75 μg/kg/min cangrelor to 4 μg/kg/min cangrelor, either with or without the 30 μg/kg bolus cangrelor dose.

Those of ordinary skill in the art will recognize that many modifications and variations of the present invention may be implemented without departing from the spirit or scope of the invention. Thus, it is intended that the present invention cover the modification and variations of this invention provided they come within the scope of the appended claims and their equivalents.

What is claimed is:

1. A method of transitioning a patient in need thereof from administration of cangrelor during percutaneous coronary intervention (PCI) to administration of cangrelor in preparation for surgery, the method comprising:
    (1) administering a PCI dosing regimen, wherein the PCI dosing regimen comprises (i) administering intravenously a 30 μg/kg bolus of cangrelor before the start of PCI; and (ii) administering intravenously a continuous infusion of cangrelor at an infusion rate of 4 μg/kg/min after administration of the bolus;
    (2) discontinuing the administration of the PCI dosing regimen; and
    (3) administering a bridge dosing regimen, wherein the bridge dosing regimen comprises administering intravenously a continuous infusion of cangrelor at an infusion rate of 0.75 μg/kg/min.

2. The method of claim 1, wherein the bolus is administered in less than one minute.

3. The method of claim 1, wherein the administration of the continuous infusion at the infusion rate of 4 μg/kg/min is started immediately after the administration of the bolus.

4. The method of claim 1, wherein the cangrelor administered as the bolus is in a pharmaceutical composition comprising 200 μg/mL of cangrelor.

5. The method of claim 1, wherein the cangrelor administered as the continuous infusion at the infusion rate of 4 μg/kg/min is in a pharmaceutical composition comprising 200 μg/mL of cangrelor.

6. The method of claim 1, wherein the cangrelor administered as the continuous infusion at the infusion rate of 0.75 μg/kg/min is in a pharmaceutical composition comprising 200 μg/mL of cangrelor.

7. The method of claim 1, wherein the bridge dosing regimen is administered as quickly as possible following the discontinuation of the administration of the PCI dosing regimen.

8. The method of claim 1, wherein the discontinuation of the PCI dosing regimen and the administration of the bridge dosing regimen is achieved simultaneously by lowering the 4 μg/kg/min infusion rate to the 0.75 μg/kg/min infusion rate.

9. The method of claim 1, wherein the administration of the bridge dosing regimen is discontinued at least about one hour prior to administration of anesthesia for the surgery.

10. The method of claim 1, wherein administration of the bridge dosing regimen is discontinued after no longer than about 7 days from initiation of the bridge dosing regimen.

11. A method of transitioning a patient in need thereof from administration of cangrelor in preparation for surgery to administration of cangrelor during percutaneous coronary intervention (PCI), the method comprising:
    (1) administering a bridge dosing regimen, wherein the bridge dosing regimen comprises administering intravenously a continuous infusion of cangrelor at an infusion rate of 0.75 μg/kg/min;
    (2) discontinuing the administration of the bridge dosing regimen; and
    (3) administering a PCI dosing regimen, wherein the PCI dosing regimen comprises (i) administering intravenously a 30 μg/kg bolus of cangrelor before the start of PCI; and (ii) administering intravenously a continuous infusion of cangrelor at an infusion rate of 4 μg/kg/min.

12. The method of claim 11, wherein the cangrelor administered as the continuous infusion at the infusion rate of 4 μg/kg/min is in a pharmaceutical composition comprising 200 μg/mL of cangrelor.

13. The method of claim 11, wherein the bolus is administered in less than one minute.

14. The method of claim 11, wherein the administration of the continuous infusion of cangrelor at the infusion rate of 4 µg/kg/min is started immediately after the administration of the bolus.

15. The method of claim 11, wherein the discontinuation of the bridge dosing regimen and the administration of the PCI dosing regimen is achieved simultaneously by administering the bolus and increasing the 0.75 µg/kg/min infusion rate to the 4 µg/kg/min infusion rate.

16. The method of claim 11, wherein the cangrelor administered as the continuous infusion at the infusion rate of 0.75 µg/kg/min is in a pharmaceutical composition comprising 200 µg/mL of cangrelor.

17. The method of claim 11, wherein the cangrelor administered as the bolus is in a pharmaceutical composition comprising 200 µg/mL of cangrelor.

18. A method of transitioning a patient in need thereof from administration of cangrelor in preparation for surgery to administration of cangrelor during percutaneous coronary intervention (PCI), the method comprising:
(1) administering a bridge dosing regimen, wherein the bridge dosing regimen comprises administering intravenously a continuous infusion of cangrelor at an infusion rate of 0.75 µg/kg/min;
(2) discontinuing the administration of the bridge dosing regimen; and
(3) administering a PCI dosing regimen, wherein the PCI dosing regimen comprises administering intravenously a continuous infusion of cangrelor at an infusion rate of 4 µg/kg/min during PCI.

19. The method of claim 18, wherein the discontinuation of the bridge dosing regimen and the administration of the PCI dosing regimen is achieved simultaneously by increasing the 0.75 µg/kg/min infusion rate to the 4 µg/kg/min infusion rate.

20. The method of claim 18, wherein the cangrelor administered as the continuous infusion at the infusion rate of 0.75 µg/kg/min is in a pharmaceutical composition comprising 200 µg/mL of cangrelor.

21. The method of claim 18, wherein the cangrelor administered as the continuous infusion at the infusion rate of 4 µg/kg/min is in a pharmaceutical composition comprising 200 µg/mL of cangrelor.

22. A method of transitioning a patient in need thereof from administration of cangrelor in preparation for surgery to administration of cangrelor during percutaneous coronary intervention (PCI), wherein the patient was being treated with a long-acting irreversible $P2Y_{12}$ inhibitor that was discontinued prior to administration of cangrelor in preparation for surgery, the method comprising:
(1) administering a bridge dosing regimen, wherein the bridge dosing regimen comprises administering intravenously a continuous infusion of cangrelor at an infusion rate of 0.75 µg/kg/min;
(2) discontinuing the administration of the bridge dosing regimen; and
(3) administering a PCI dosing regimen, wherein the PCI dosing regimen comprises (i) administering intravenously a 30 µg/kg bolus of cangrelor before the start of PCI; and (ii) administering intravenously a continuous infusion of cangrelor at an infusion rate of 4 µg/kg/min.

23. The method of claim 22, wherein the cangrelor administered as the bolus is in a pharmaceutical composition comprising 200 µg/mL of cangrelor.

24. The method of claim 22, wherein the cangrelor administered as the continuous infusion at the infusion rate of 4 µg/kg/min is in a pharmaceutical composition comprising 200 µg/mL of cangrelor.

25. The method of claim 22, wherein the bolus is administered in less than one minute.

26. The method of claim 22, wherein the administration of the continuous infusion of cangrelor at the infusion rate of 4 µg/kg/min is started immediately after the administration of the bolus.

27. The method of claim 22, wherein the discontinuation of the bridge dosing regimen and the administration of the PCI dosing regimen is achieved simultaneously by administering the bolus and increasing the 0.75 µg/kg/min infusion rate to the 4 µg/kg/min infusion rate.

28. The method of claim 22, wherein the cangrelor administered as the continuous infusion at the infusion rate of 0.75 µg/kg/min is in a pharmaceutical composition comprising 200 µg/mL of cangrelor.

* * * * *